(12) United States Patent
Romo

(10) Patent No.: US 12,178,731 B1
(45) Date of Patent: Dec. 31, 2024

(54) ARTICULATED ANKLE FOOT ORTHOSIS

(71) Applicant: Aspen Medical Products, LLC, Irvine, CA (US)

(72) Inventor: Harry Duane Romo, Irvine, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 309 days.

(21) Appl. No.: 17/840,270

(22) Filed: Jun. 14, 2022

Related U.S. Application Data

(60) Provisional application No. 63/210,831, filed on Jun. 15, 2021.

(51) Int. Cl.
*A61F 5/01* (2006.01)
*A61F 2/68* (2006.01)
*A61F 2/70* (2006.01)
*A61F 2/76* (2006.01)

(52) U.S. Cl.
CPC .............. *A61F 5/0127* (2013.01); *A61F 2/68* (2013.01); *A61F 5/0111* (2013.01); *A61F 2002/701* (2013.01); *A61F 2002/7625* (2013.01)

(58) Field of Classification Search
CPC ........ A61F 5/0127; A61F 5/0102; A61F 5/01; A61F 5/00; A61F 5/0111; A61F 2005/0165; A61F 2005/0169; A61F 2005/0153; A61F 2005/0137; A61F 2005/0132; A61F 2005/0179; A61F 2/68; A61F 2002/701; A61F 2002/7625

USPC ............................ 602/5, 16, 23, 27; 128/882
See application file for complete search history.

(56) References Cited

U.S. PATENT DOCUMENTS

| | | | |
|---|---|---|---|
| 6,530,868 B1 * | 3/2003 | Pape | A63B 21/0004 482/127 |
| 10,470,914 B2 | 11/2019 | Powell et al. | |
| 2018/0289524 A1 | 10/2018 | Takeda et al. | |

FOREIGN PATENT DOCUMENTS

| | | | | |
|---|---|---|---|---|
| WO | 2009015473 A1 | 2/2009 | | |
| WO | WO-2020083696 A1 * | 4/2020 | ............... | A61F 2/60 |

OTHER PUBLICATIONS

PCT/US2022/033618 filed Jun. 15, 2022 International Search Report and Written Opinion dated Nov. 2, 2022.

* cited by examiner

Primary Examiner — Caitlin A Carreiro
(74) Attorney, Agent, or Firm — Rutan & Tucker, LLP

(57) ABSTRACT

The inventive subject matter provides apparatus, systems and methods in which an ankle foot orthosis (AFO) utilizes a rotary jaw coupling that prevents excessive plantarflexion and dorsiflexion of the foot, while still allowing such movements with little or no counterforce over a limited range. The jaw coupling comprises at least a first digit which is freely or almost freely rotatable between first and second stops in the range of 30° to 60° of arc, and more preferably between 30° to 40° of arc. Extreme motion of the digit(s) is limited by one or more stops. Different ranges of motion can be provided by replaceable spiders. Resilient materials can be used to provide desired characteristics of resiliency, compressibility, damping, and/or amounts of play.

29 Claims, 16 Drawing Sheets

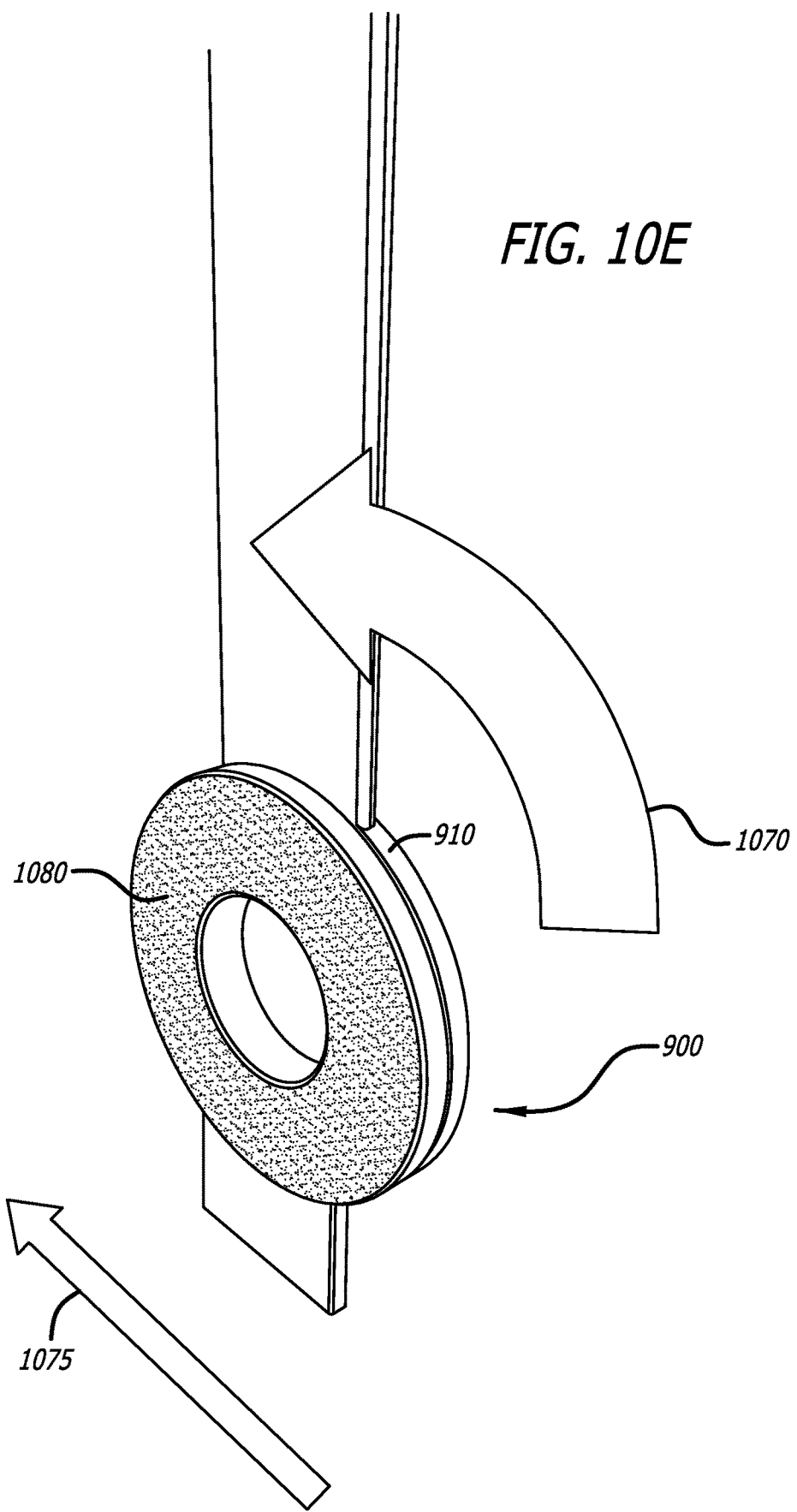

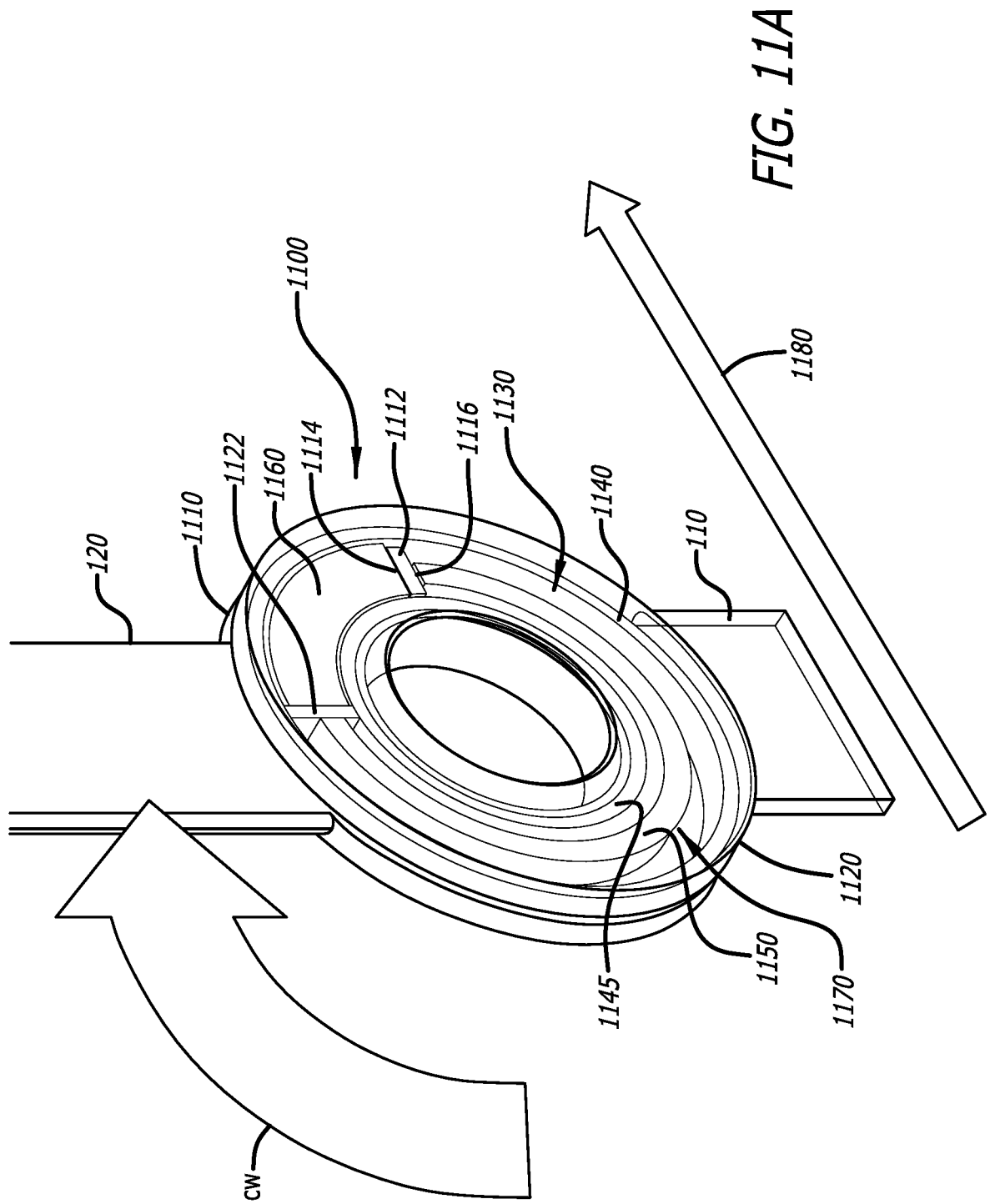

ARTICULATED ANKLE FOOT ORTHOSIS

CROSS-REFERENCE TO RELATED APPLICATIONS

This application claims priority to U.S. Provisional Patent Application No. 63/210,831 filed Jun. 15, 2021, the entire contents of which is incorporated by reference herein.

FIELD

The field of the invention is ankle foot orthoses.

BACKGROUND

The following description includes information that may be useful in understanding the present invention. It is not an admission that any of the information provided herein is prior art or relevant to the presently claimed invention, or that any publication specifically or implicitly referenced is prior art.

An ankle foot orthosis (AFO) is one of the most common, non-surgical solutions for a patient who is suffering from foot drop or other walking disorders. AFOs are designed to provide support of, and proper joint alignment between, the foot and ankle during use.

Currently, available AFOs use a spring or elastic material to provide a counterforce against excessive or otherwise undesirable plantarflexion or dorsiflexion. For example, WIPO Application No. WO01/35876 describes an AFO having a spring running along the anterior of the lower leg, ankle, and dorsum of the foot. U.S. patent Ser. No. 10/682,249 describes a knee orthosis having a spring positioned between an upper leg and a lower leg. These springs operate at all ranges of motion to maintain the leg and foot at a neutral or other predetermined angulation. All publications herein are incorporated by reference to the same extent as if each individual publication or patent application were specifically and individually indicated to be incorporated by reference.

The Push™ Ortho™ AFO Ankle Foot Orthosis accomplishes a similar effect with elastic material that wraps about the lower leg, ankle, and foot. Still other devices use pneumatics to maintain the leg and foot at a neutral or other predetermined angulation. See, e.g., "Mechanics and energetics of level walking with powered ankle exoskeletons," The Journal Of Experimental Biology, 2008, 1402-1413.

One possible problem with these prior art devices is that any movement of the foot is immediately opposed by a counterforce. Accordingly, there is no free motion of the foot relative to the lower leg, and that lack of free motion can interfere with proper gait.

Thus, there is still a need for an ankle foot orthosis (AFO) that prevents excessive plantarflexion and dorsiflexion of the foot, while still encouraging proper gait by fine tuning counterforce to plantarflexion and dorsiflexion over a limited range.

SUMMARY

Embodiments of the inventive subject matter is directed to an apparatus, system, and method in which an ankle foot orthosis (AFO) utilizes a hinge, represented as a rotary jaw coupling for example, that prevents excessive plantarflexion and dorsiflexion of the foot while still allowing plantarflexion and dorsiflexion with little or no counterforce over a limited range. The prevention of excessive plantarflexion and dorsiflexion of the foot may be accomplished through resiliently compressible material such as a coating, a dampener, a spring, or an insert between the jaw coupling (referred to herein as a "spider").

According to one embodiment of the disclosure, the hinge comprises a first hinge member rotationally coupled to a second hinge member. Each of the hinge members includes one or more protrusions operating as digits or stops. Herein, according to this embodiment of the disclosure, the first hinge member features at least a first digit, where the first hinge member is freely or almost freely rotatable between the first and second stops of the second hinge member in the range between zero and ninety degrees of arc (0°-90°) of arc, such as angular ranges of 300 to 600 of arc, and more preferably between 300 to 400 of arc. Motion of the digit(s) may be limited by one or more stops and/or by resistance applied from resiliently compressible material positioned between rotatable digit(s) and corresponding stop(s). The resiliently compressible material may include (i) one or more dampeners (e.g., material with a selected durometer, namely a selected level of rigidity in order to provide a desired amount of resistance) positioned within an area between at least one digit (e.g., protrusion positioned within a housing of the lateral member) and a neighboring stop (e.g., protrusion positioned within a housing of the medial member) or (ii) e a spring made of a composite material (e.g., carbon fiber, fiberglass, etc.).

As used herein, the term "freely or almost freely" with respect to rotation or other movement over a range of motion means that there is less than a predetermined amount of force applied against the movement ("counterforce") over that range of motion. Examples of predetermined amount of force include, but are not limited to, 0.5 Newtons, 1 Newton, 2 Newtons, 5 Newtons, 10 Newtons, 20 Newtons, or the like. The amount of counterforce may be used to control dorsiflexion and/or plantarflexion, where the amount of control may preclude movement of a patient's ankle and/or foot to provide a cast-like operability or the amount of control may assist in resisting (and thereby slowing) tibial progression and/or preventing foot slap normally caused by weakness of the foot and ankle dorsiflexors in which the foot slaps down on the floor with each step.

As described below, in some embodiments, movement(s) of the digit(s) may be attenuated by a resiliently compressible material. All suitable types and sizings of material are contemplated, including deploying the materials as dampeners or springs with different durometers (i.e., measures or levels of rigidity) and/or different sizes to control different levels or resistance against (and control of) dorsiflexion and/or plantarflexion. Additionally, all suitable locations for such material are contemplated such as dampeners or springs inserted between the digits and stops as described above, or as a coating onto one or more of the digits, and/or one or more of the stops. The resiliently compressible material can also be provided as, or on, a spider positioned between digits and stops.

As used herein, the term "resiliently compressible" with respect to an object or portion of an object means that the object deforms under force, and generally returns to a pre-force structure after releasing of the force. In some embodiments of the disclosure, some contemplated resiliently compressible materials can operate as dampeners to provide a structural damping effect to movement of the digit(s). Such damping can be advantageously used to provide a desired cushioning while allowing motion. Differing amounts of damping can be adjusted by using different materials for the dampeners or composite spring(s). Amount of damping can be expressed by a damping coefficient, where the damping coefficient may be as large to prevent movement, as small to allow for free (but guided) motion, or some intermediary degree of movement sufficient to provide some control as to dorsiflexion and/or plantarflexion.

As used herein, the term "play" means an amount of motion that an object can move against a compressible material. For example, if a digit of a jaw coupling can move 1 millimeter (mm) after first touching a compressible stop, then the play is 1 mm.

Adjustment or customization to the needs of a particular patient or other user can be accomplished in many ways, all of which can advantageously accomplished using replaceable spiders. Different spiders, for example, can produce different ranges of motion, and can have different resiliency, different compressibility, different damping characteristics, and different amounts of play.

As used herein, and unless the context dictates otherwise, the term "coupled" and other tenses thereof are intended to include both direct coupling (in which two elements that are coupled to each other contact each other) and indirect coupling (in which at least one additional element is located between the two elements). Therefore, the terms "coupled to" and "coupled with" are used synonymously.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps, or acts are in some way inherently mutually exclusive.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 10E is a perspective view of the assembled hinge of FIGS. 10A-10C identifying movement in response to ambulatory movement by a patient.

FIG. 11A is a perspective view of a third embodiment of a hinge (jaw coupling) of the AFO of FIG. 1, including a C-shaped composite spring deployed within the second hinge (medial) member.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The recitation of ranges of values herein is merely intended to serve as a shorthand method of referring individually to each separate value falling within the range. Unless otherwise indicated herein, each individual value is incorporated into the specification as if it were individually recited herein. Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claim.

I. AFO with First Hinge Embodiment

Figure 1:
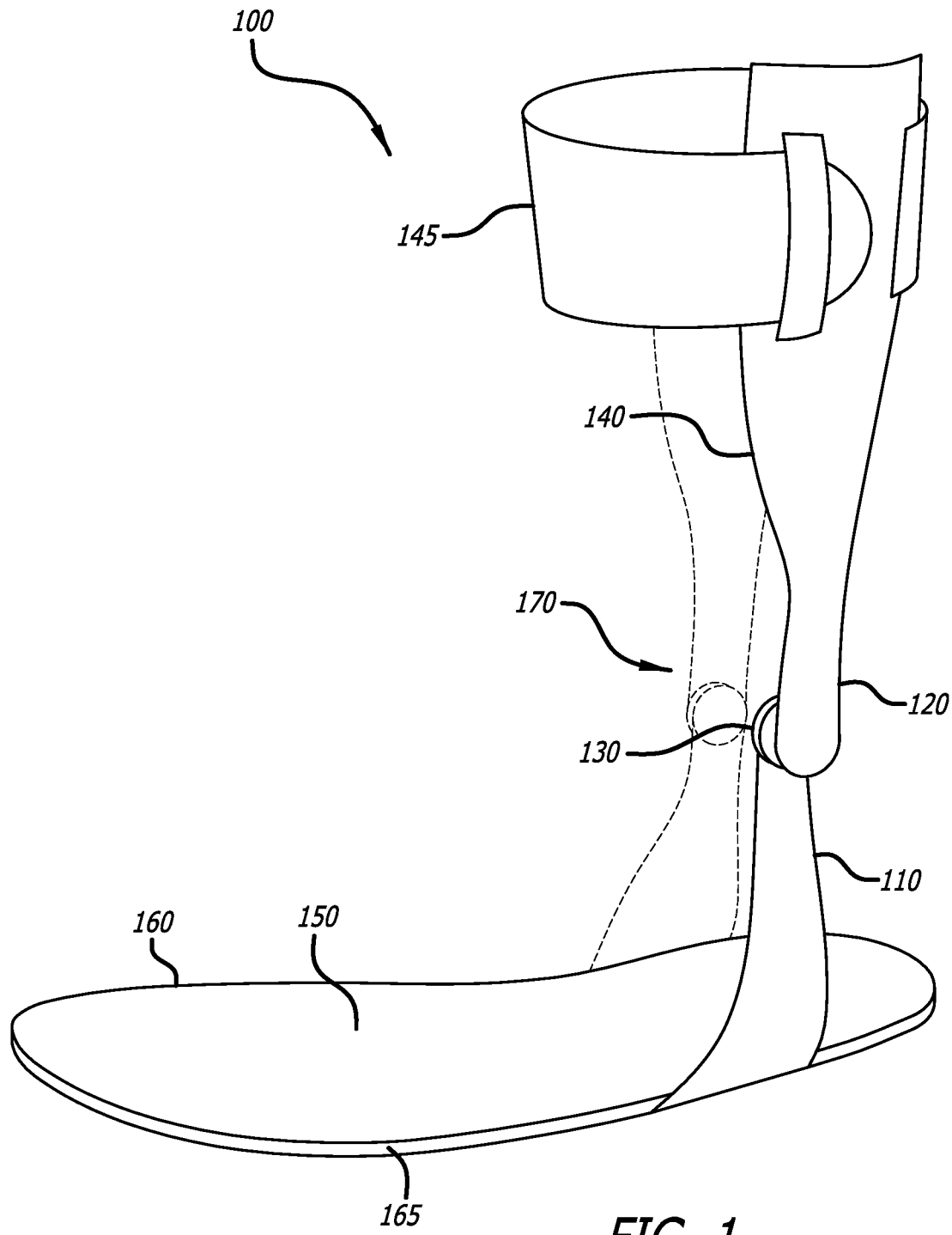
FIG. 1 is a perspective view of an ankle foot orthosis (AFO) illustrative of a single-hinge AFO configuration demonstrating a hinge on one side of the ankle with an optional dual-hinge configuration having hinges on both sides of the ankle.

Referring to FIG. 1, a perspective view of an illustrative embodiment of an ankle foot orthosis (AFO) is shown, Herein, the AFO 100 is configured with a foot connector 110, a lower leg connector 120, and a hinge 130 (sometimes referred to as a "jaw coupling"). The hinge 130 is interposed between the lower leg connector 120 and the foot connector 110. Optionally, as illustrated with dashed lines, the AFO 100 may be configured as a dual hinge AFO where an additional foot connector, lower leg connector and hinge 170 are positioned on an opposite width side of a foot plate 150. The dual hinge AFO would reduce an amount of load applied to the hinge 130 and provide better guidance of movement of the patient's foot along a sagittal plane and possibly avoid the patient's foot attempting to wrap around the foot connector 110.

Herein, the lower leg connector 120 is coupled with a leg cuff 140, which is positioned generally proximate to and around the calf of the patient. The leg cuff 140 may be configured with a strap 145 to attach around the calf of the patient. Additionally, the foot connector 110 is coupled to a foot plate 150 or a shoe. Although not shown, the foot plate 150 may include a strap extending from side edges 160 and 165 of the foot connector 110.

Figure 2:
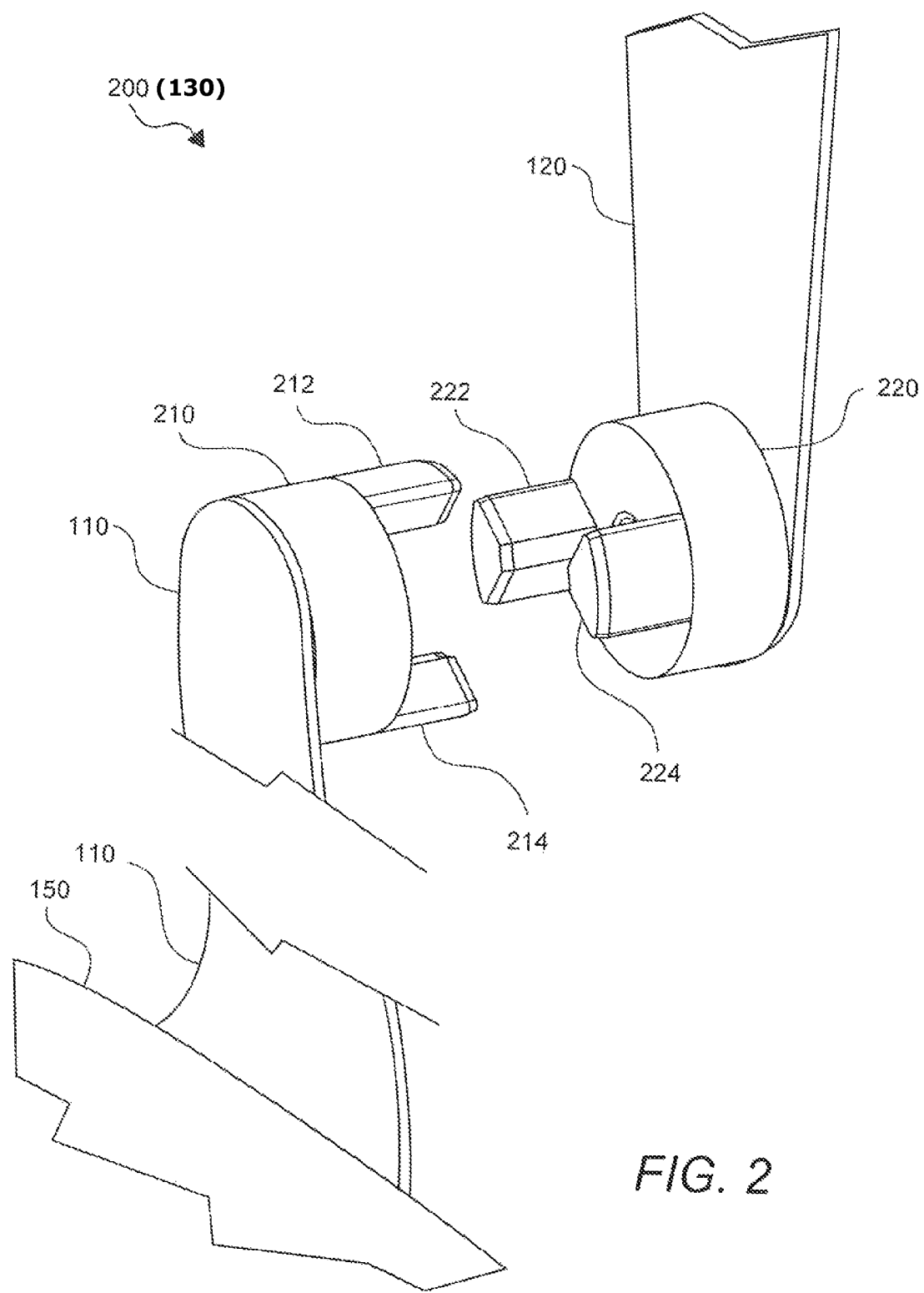
FIG. 2 is an exploded perspective view of a first embodiment of the AFO of FIG. 1, including a hinge (jaw coupling) with a plurality of digits on each of the first and second hinge members operating as lateral and medial members of the hinge for this embodiment.
Figure 9:
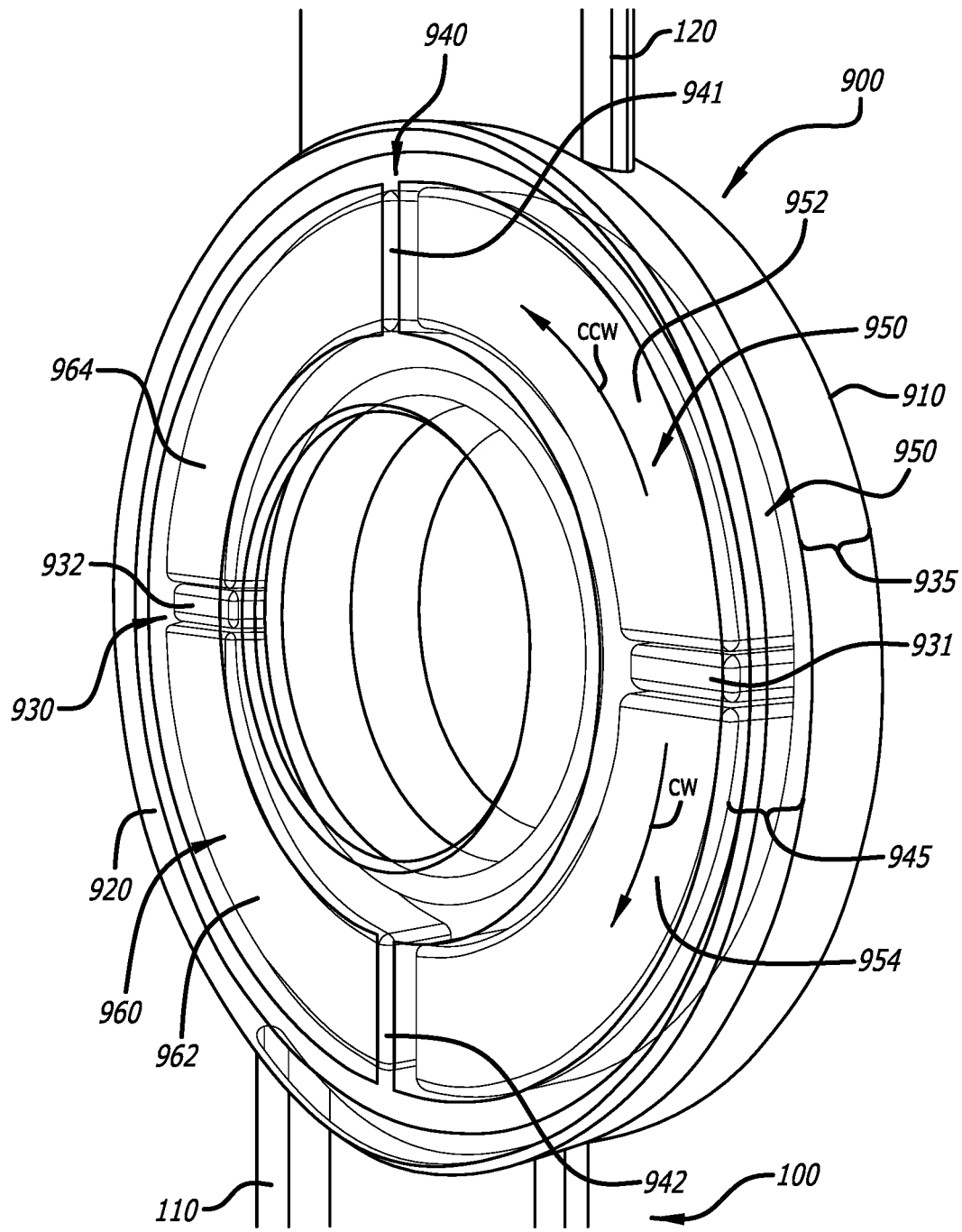
FIG. 9 is a perspective view of a second embodiment of a hinge (jaw coupling) of the AFO of FIG. 1, including a first set of digits extending from a first hinge (lateral) member for insertion into corresponding recessed areas created by dampener pairs within a housing of a second hinge (medial) member.

As shown herein and with greater detail in FIG. 2, the hinge 130 features a first hinge member and a second hinge member, where a medial member may operate as the rotational hinge member while a lateral member may operate as a static hinge member. Alternatively, as shown in FIG. 9, the hinge 130 may be configured as a first hinge member and a second hinge member, where the lateral member may operate as the rotational first hinge member while the medial member may operate as a static second hinge member. Herein, the hinge members may be referred to as medial members and lateral members, albeit the inventive features may be applicable regardless if deployed as part of the medial member (e.g., hinge member communicatively coupled to the foot connector 110 according to this embodiment) or the lateral member (e.g., the hinge member communicatively coupled to the lower leg connector 120 according to this embodiment). Stated differently, the hinge 130 could be flipped in which the medial (hinge) member may be communicatively coupled to the lower legal connector 120 while the lateral (hinge) member may be communicatively coupled to the foot connector 110. Therefore, while illustrative embodiments of the AFO hinge are described in connection with medial and lateral members, the claimed invention is directed to a first and second hinge members, irrespective as to whether these hinge members correspond to medial or lateral members.

FIG. 2 generally depicts a hinge 200, represented as a jaw coupling (corresponding to jaw coupling 130 of FIG. 1), having first hinge (medial) and second hinge (lateral) members 210, 220. The medial member 210 features a first digit (e.g., protrusion) 212 and a second digit 214, which are positioned 180 degrees apart from each other. Lateral member 220 features a third digit 222 and a fourth digit 224 also positioned 180 degrees apart, but these digits 222 and 224 are offset approximately 90 degrees from the first and second digits 212 and 214. This allows for an interlocking assembly of the medial and lateral members 210 and 220, in which the first and second digits 212 and 214 are disposed between the third and fourth digits 222 and 224, respectively.

Each of the medial and lateral members 210, 220 is rotatable relative to the other, until such time as the digits 212, 214 of the medial member 210 come in contact against digits 222, 224 of the lateral side 220. For the purposes of clarity in the following discussion, the digits 212, 214 of the medial member 210 may be referred to as "digits" while the digits 222, 224 of the lateral member 220 may be referred to as "stops".

In the example shown in FIG. 2, the subtension of the digits (maximum degrees of rotation) is the same. However, the subtension of the digits can modified by changing the number of the digits on each of the members 210, 220, and/or by changing the size of the digits and/or stops. If the orthosis needs to support stride and cadence increases that correspond to increased forces being applied to the AFO hinge, the subtension of the digits and/or stops should be larger in angular length, such that the number and/or the size of the digits and/or stops are smaller. If the orthosis needs to support stride or cadence decreases that correspond to decreased forces being applied to the AFO hinge, the subtension of the digits and/or stops should be smaller in angular length, such that the number and/or the size of the digits and/or stops are larger.

In embodiments of the inventive subject matter, the contemplated rotation of the digits between two consecutive stops with little or no counterforce is illustrative as being up to ninety (90°) degrees of arc, albeit rotations may occur between 30 and 60 degrees of arc, inclusive. In certain embodiments, the contemplated rotation of the digits between two consecutive stops with little or no counterforce may occur between 30 and 40 degrees of arc, inclusive. In other contemplated embodiments, the contemplated rotation of the digits between two consecutive stops with counterforce may occur between 40°-60° of arc, inclusive.

Referring to FIGS. 1-2, the digits and/or stops should be interpreted as comprising a material that is resiliently compressible by at least 1 degree of arc. Since a resiliently compressible material provides structural damping, this can advantageously reduce impact and backlash of the digits/stops contacting one another during walking. In some embodiments, opposite sides of the digits/stops can have different degrees of resiliency and/or compressibility, which can provide different effects upon plantarflexion and dorsiflexion during walking.

Resiliency and compressibility can be additionally or alternatively accomplished using a coating on the digits (as discussed with respect to FIG. 3), with springs acting upon the digits (as discussed with respect to FIG. 4), with the use of a spider (as discussed with respect to FIGS. 5A-7), or through dampeners and/or composite springs (as discussed with respect to FIGS. 9-11C).

Contemplated materials to provide resilient compressibility include, but are not limited to, an elastomer (e.g., rubber, etc.) foam, and plastic. Suitable contemplated resiliency ranges and compressibility ranges from will depend on factors including, but not limited to, the desired range of motion and size of the coupling and/or the size of the orthosis device itself. Likewise, suitable damping coefficients provided by the materials may depend on these and other factors as well.

Figure 3:
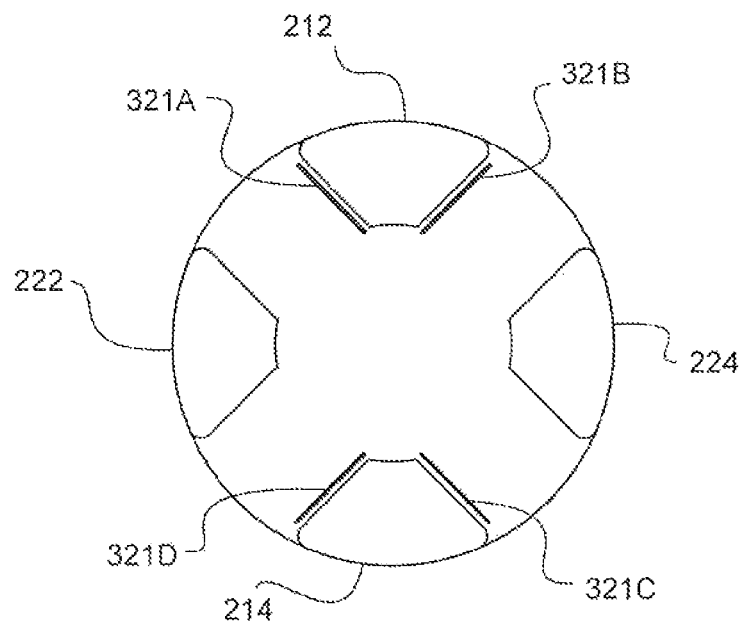
FIG. 3 is a cross-sectional perspective view of a first embodiment of the hinge (jaw coupling) of FIG. 2 that incorporates a resiliently compressible coating.

FIG. 3 is a cross-sectional perspective view of an assembled jaw coupling that incorporates a resiliently compressible coating, according to embodiments of the inventive subject matter. As seen in FIG. 3, resiliently compressible coating 321A, 321B, 321C, and 321D is appended on each side of the digits 212 and 214. It should be noted that the coating can also be applied to the stops 222, 224 in addition to or instead of the digits 212, 214. The coating 321A-321D can be applied in addition to the compressibility discussed above for the actual digits 212, 214 and stops 222, 224. In other embodiments, the compressible coating 321A-321D can be applied where the digits 212, 214 and stops 222, 224 are not compressible or deformable.

In embodiments of the inventive subject matter, the compressible coating 321A-321D is moveable relative to one or more of a digit and one or both of the stops on either side of the digit.

Figure 4:
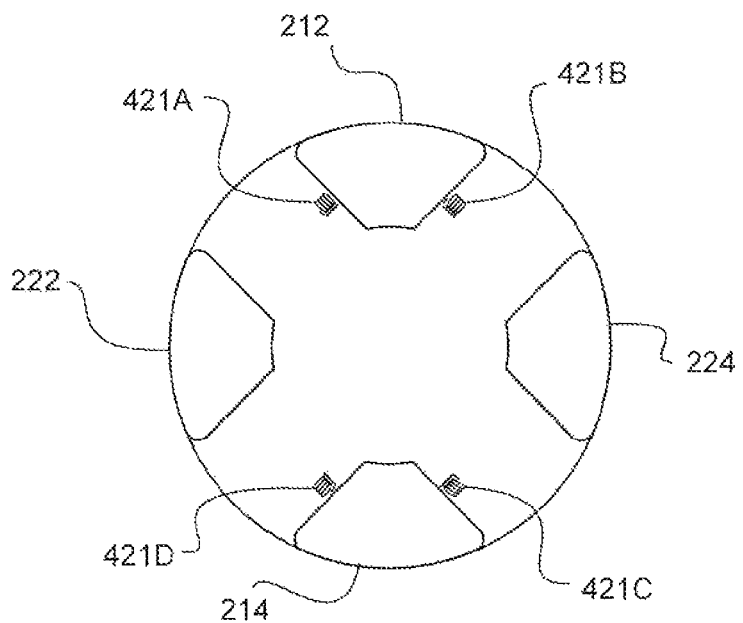
FIG. 4 is a cross-sectional perspective view of a second embodiment of the hinge (jaw coupling) of FIG. 2, depicting the use of springs as the resiliently compressible material.

FIG. 4 is a cross-sectional perspective view of another assembled jaw coupling, depicting the use of springs 421A-421D as the resiliently compressible material, according to embodiments of the inventive subject matter. As seen in FIG. 4, the springs 421A-421D are positioned on the digits, between the digits 212, 214 and the stops 222, 224. It should be noted that springs 421A-421D can be positioned on any of the digits and/or stops.

In embodiments of the inventive subject matter, the resiliently compressible material on either side of a digit 212, 214 (including the embodiments depicting a coating in FIG. 3 and springs in FIG. 4) is such that the amount of play provided on either side of the digit 212, 214 due to the material is different for the same amount of force applied. For example, in the embodiment of FIG. 4, spring 421A between the digit 212 and the stop 222 could have a different spring tension than a spring 421B between the digit 212 and stop 224. Therefore, for a given force applied, the amount of play in the direction of the stop 222 would be different than the amount of play for the same force in the direction of the stop 224.

In embodiments of the inventive subject matter, the resiliently compressible material on either side of a digit can have different hysteresis of compression for the same amount of force. Spring 421A between the digit 212 and the stop 222 could have a different hysteresis of compression than a spring 421B between the digit 212 and stop 224.

Figure 5A:
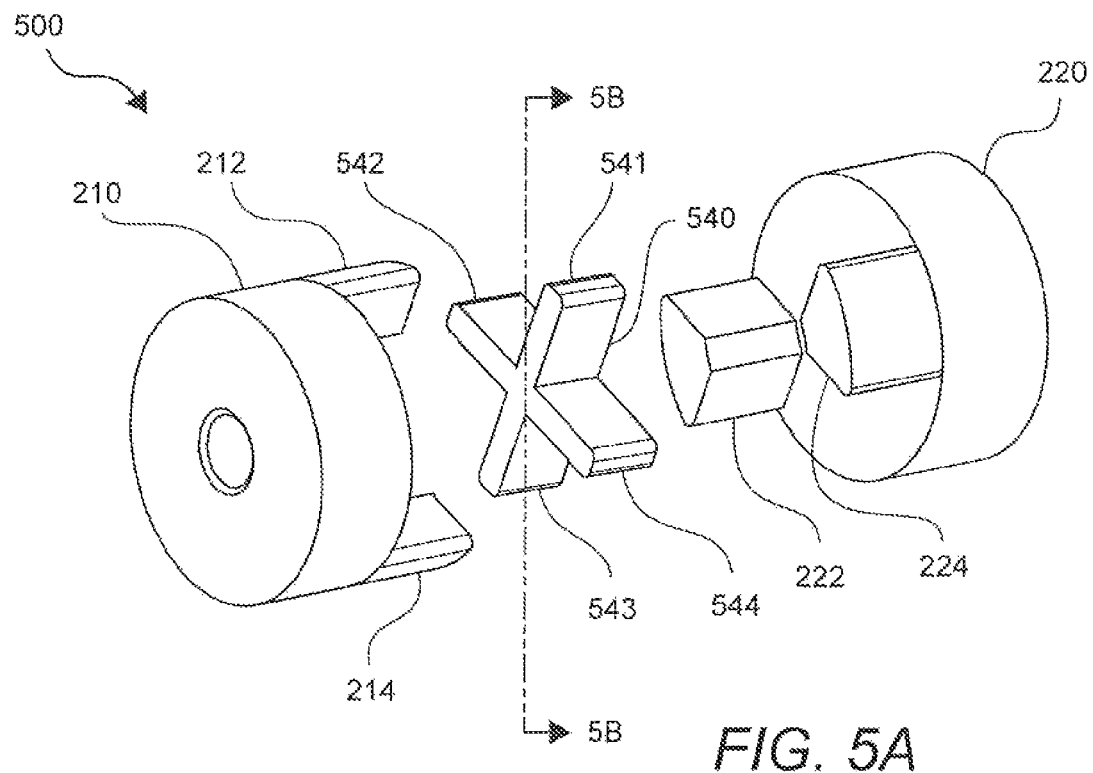
FIG. 5A is an exploded perspective view of a second embodiment of the AFO of FIG. 1, including a hinge (jaw coupling) having an insert (spider) with extending segment (arms) oriented to fit among the lateral and medial members.
Figure 5B:
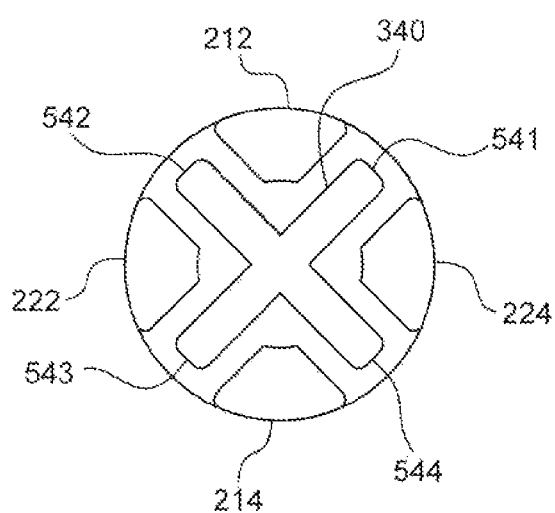
FIG. 5B is a cross-sectional perspective view of the assembled hinge (jaw coupling) of FIG. 5A.

FIG. 5A generally depicts a jaw coupling 500 having medial and lateral members 210, 220 with an insert (referred to as a "spider") 540 having four arms 541, 542, 543, 544. FIG. 5B generally depicts a vertical cross-section 5B-5B of assembled jaw coupling 300 shown in FIG. 5A. In the assembled jaw coupling 300, the spider arms 541, 542, 543, 544 are positioned respectively between consecutive digits and stops 212, 224, 214, 222.

In some embodiments, the arms 541, 542, 543, 544 can be resiliently compressible, and as discussed above with respect to digits/stops, opposing sides of the arms can have different degrees of resiliency and compressibility.

Spiders can be user- or medical personnel-replaceable to provide adjustments for range of motion, resiliency, compressibility, damping characteristics, and amounts of play.

Addition of spider arms between the digits and stops automatically narrows the degree of the subtension of the digits and stops. Accordingly, the digits/stops of jaw couplings with spiders will be likely to be fewer in number and/or narrower than digits/stops of jaw couplings used without spiders. It is also contemplated one or more individual spacers (e.g., dampener(s), spring(s), composite spring, coating, and/or any material or structure with dampening characteristics) could be used instead of the arms of a spider.

Figure 6:
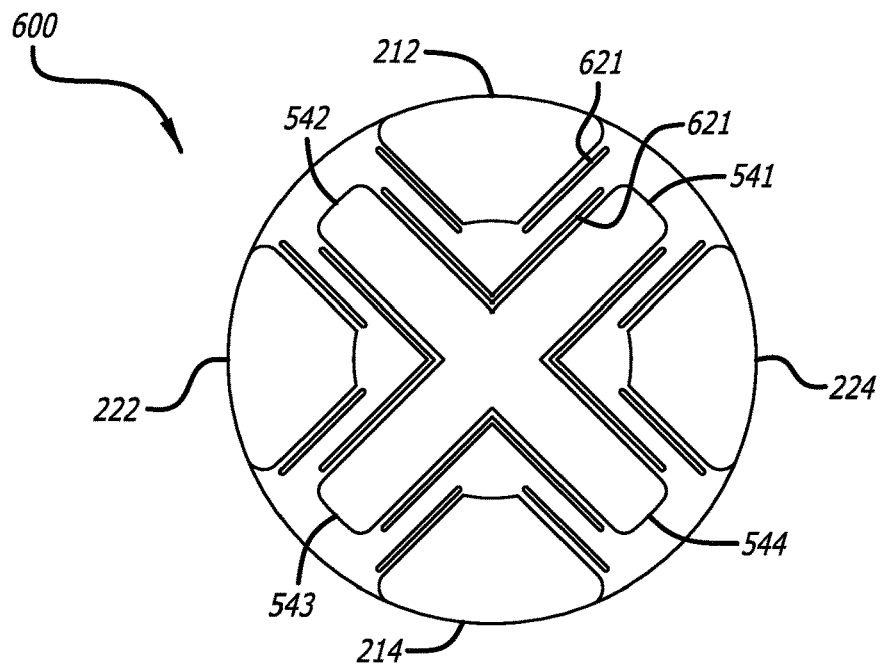
FIG. 6 is a cross-sectional perspective view of a first embodiment of the assembled hinge (jaw coupling) of FIG. 5A, depicting resiliently compressible coating on the digits and the spider arms.

FIG. 6 is a cross-sectional perspective view of a different assembled hinge (jaw coupling) 600, depicting resiliently compressible coating 621 on the digits and the spider arms 541, 542, 543, 544. The coating 621 can be positioned on any of the digits and/or spider arms. The coating 621 can be applied in addition to the compressibility discussed above for the actual digits 212, 214 and stops 222, 224. In other embodiments, the compressible coating 621 can be applied where the digits and stops are rigid and not compressible or deformable.

In embodiments of the inventive subject matter, the compressible coating 621 is moveable relative to one or more of a digit and one or both of the stops on either side of the digit.

Figure 7:
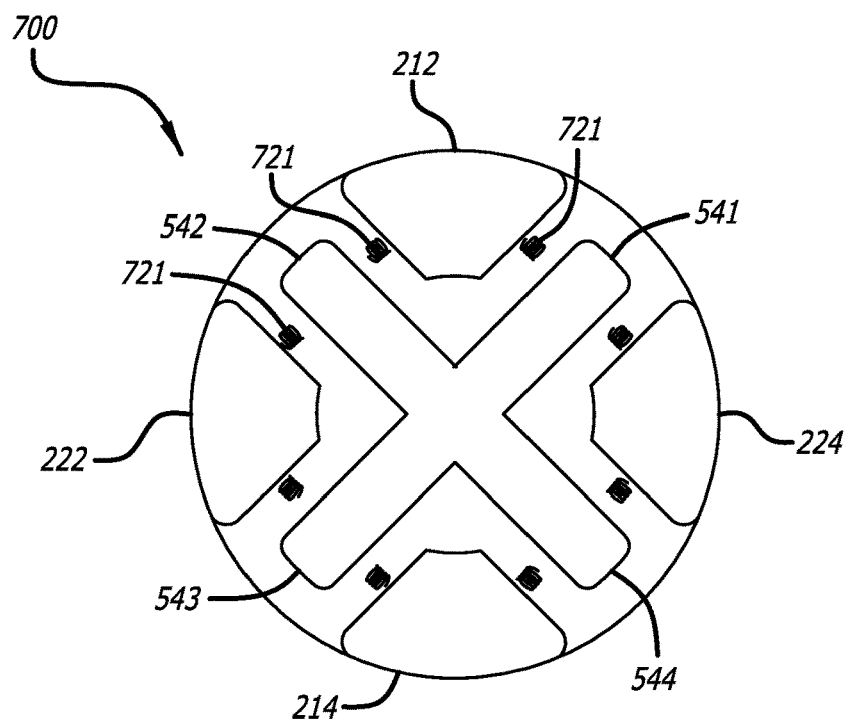
FIG. 7 is a cross-sectional perspective view of a second embodiment of the assembled hinge (jaw coupling) of FIG. 5A, depicting springs between the digits and the spider arms.

FIG. 7 is a cross-sectional perspective view of yet another assembled hinge (jaw coupling) 700, depicting the use of springs 721 as the resiliently compressible material. As seen in FIG. 7, the springs 721 are positioned between the spider arms 541, 542, 543, 544 and the adjacent digit and stop. Springs 721 can be positioned on any of the digits and/or spider arms.

Figure 8:
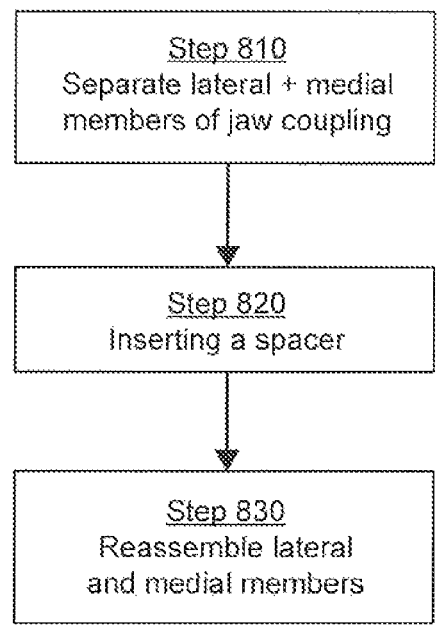
FIG. 8 is an exemplary flowchart depicting a method of adjusting an ankle foot orthosis (AFO) to a recipient.

FIG. 8 is a flowchart illustrating a method 800 of adjusting an ankle foot orthosis to a recipient, the orthosis having a jaw coupling functionally interposed between a lower leg connector and the foot connector, and having at least a first digit moveable between first and second stops, including the steps of: Separating the lateral and medial members of the jaw coupling (hinge) at step 810.

At step 820, inserting a first spacer between the first digit and the first stop, a second spacer between the second digit and the second stop.

At step 830, reassembling the lateral and medial members of the jaw coupling.

In embodiments of the inventive subject matter, the method can further include one or more of the following operations:

1. Determining an amount of free movement and/or resistance provided by an AFO hinge including a first hinge member and a second hinge member to prevent excessive plantarflexion and/or dorsiflexion of a patient's foot when wearing the AFO;
2. Selecting one or more spacers (e.g., dampener(s), spring(s), composite spring, coating, and/or any material or structure with dampening characteristics), such as a first and second spacers, to achieve a desired resilient compressibility in the AFO hinge;
3. Inserting the one or more spacers within an area provided by the second hinge member;
4. Having a first digit extending from a surface of the first hinge member inserted between and moveable to engage with the one or more spacers in response to rotational movement of the first hinge member in relation to the second hinge member, where the first digit experiences resistance caused by a spacer during rotation to control an amount of plantarflexion and dorsiflexion; and
5. Substituting the one or more spacers for different types of spacers based on type of activity.

II. AFO with Second Hinge Embodiment

Referring to FIG. 9, a perspective view of a second embodiment of a hinge 900 (jaw coupling 130) of the AFO 100 of FIG. 1 is shown. As shown, the hinge 900 includes a first hinge member 910 and a second hinge member 920. The second hinge member 920 operates as a lower hinge portion of the AFO 100 and may be deployed as a medial member attached to the foot connector 110. The first hinge member 910 operates as an upper hinge portion of the AFO 100 and may be deployed as a lateral member attached to the lower leg connector 120. When the AFO 100 is worn, as the first and second hinge members 910 and 920 articulate, the biomechanical properties of the AFO 100 control the relationship between the patient's shin and foot. Herein, the hinge 900 includes internal components that can be changed, replaced, added, or removed to alter the biomechanical properties of the AFO 100.

The first hinge member 910 features an interior area, including a first set of digits 930 (e.g., digits 931 and 932 positioned within a housing 935 being an interior area of the first hinge member 910. As shown, the first set of digits 930 may be positioned on diametrically opposite sections of the housing 935. As shown, the positioning of digits 931 and 932 is maintained at 3 o'clock and 9 o'clock locations, albeit other locations are considered (e.g., 2:00/8:00; 1:30/7:30; 4:00/10:00, etc.). Of course, it is contemplated that the first set of digits 930 may feature any number of digits (e.g., three or more digits) uniformly spaced along a perimeter of the housing 935 of the first hinge member 910. According to one embodiment of the disclosure, the housing 935 is formed as one or more recessed areas (e.g., channels) adapted to assist in encapsulating and/or retaining one or more dampeners made of resiliently compressible material between at least digits 931 and 932.

Figure 10A:
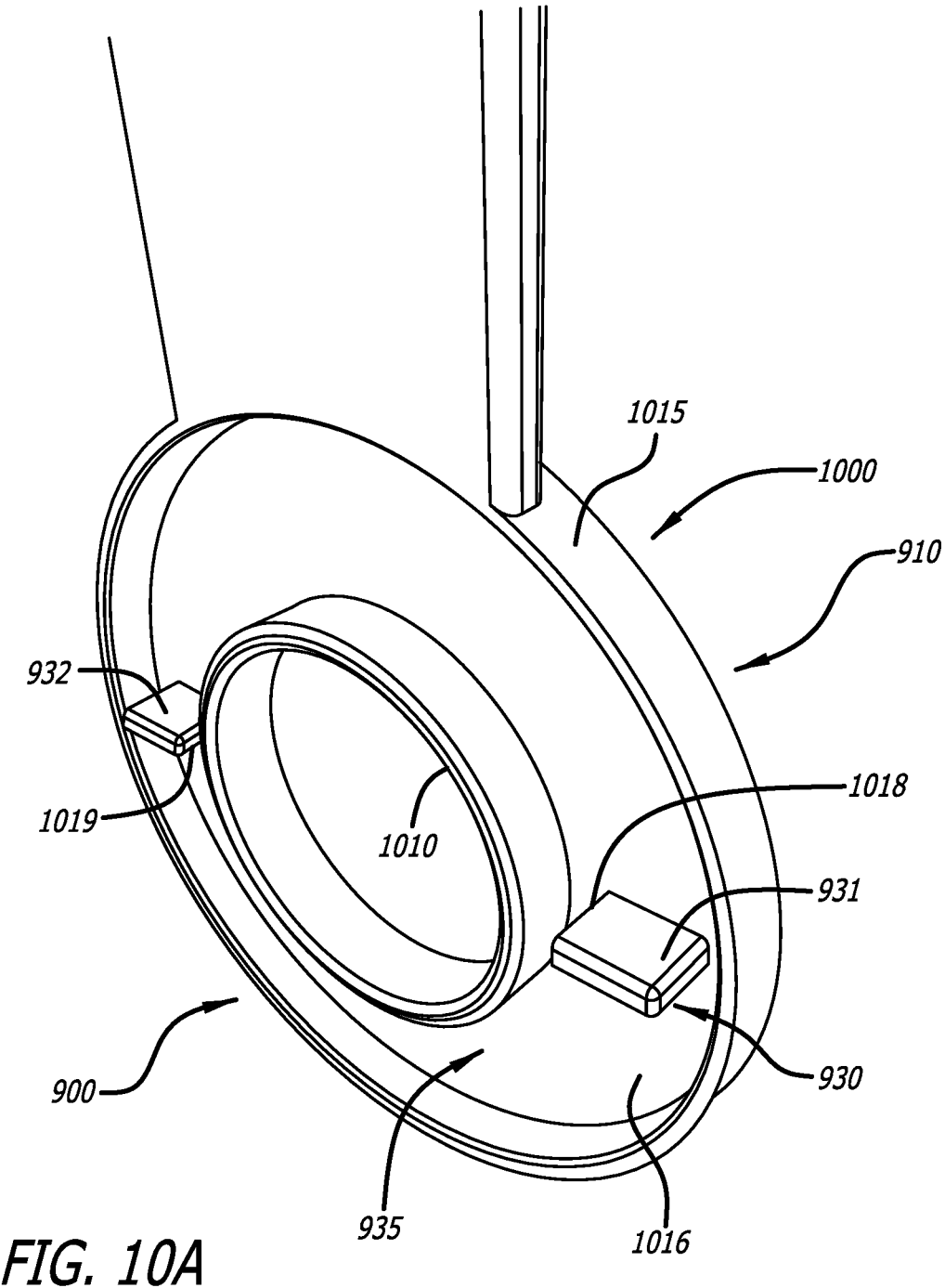
FIG. 10A is a perspective view of an embodiment of the first hinge member of FIG. 9.
Figure 10B:
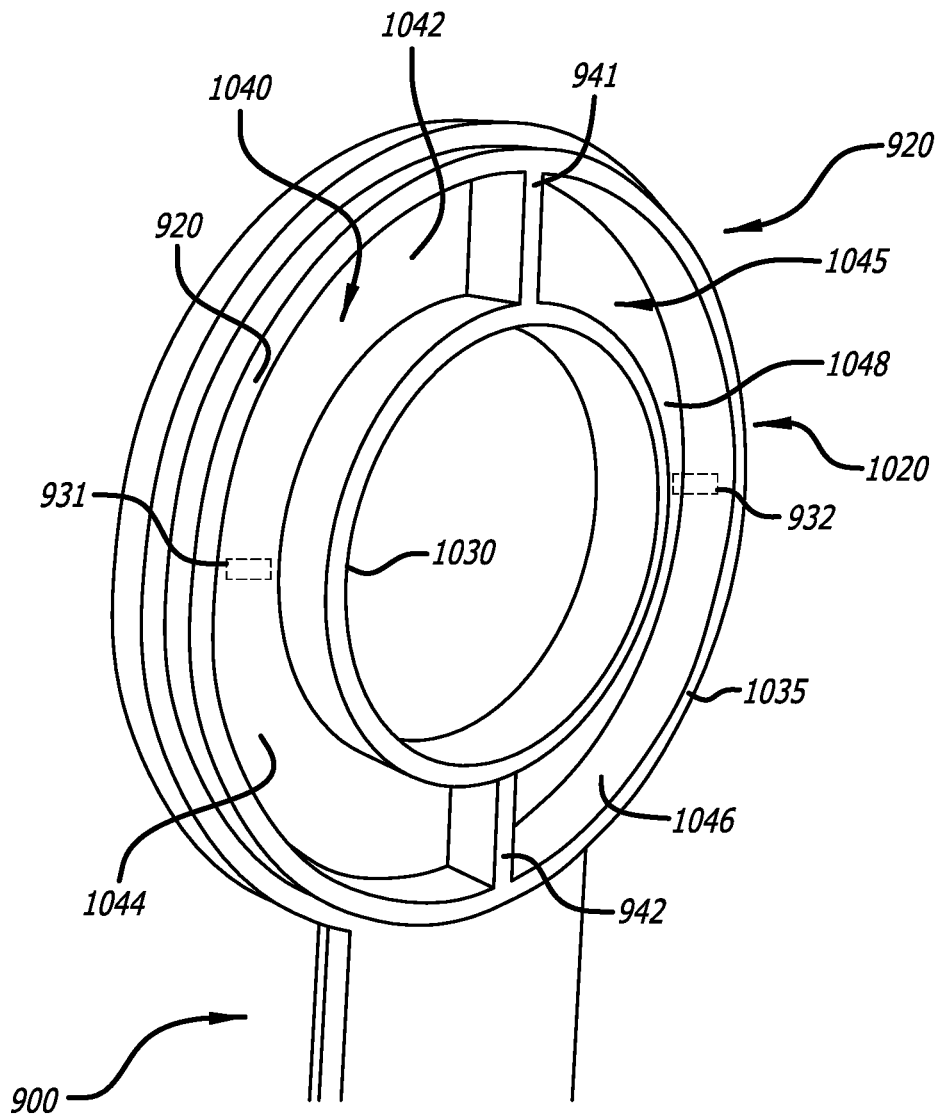
FIG. 10B is a perspective view of an embodiment of the second hinge member of FIG. 9.
Figure 10C:
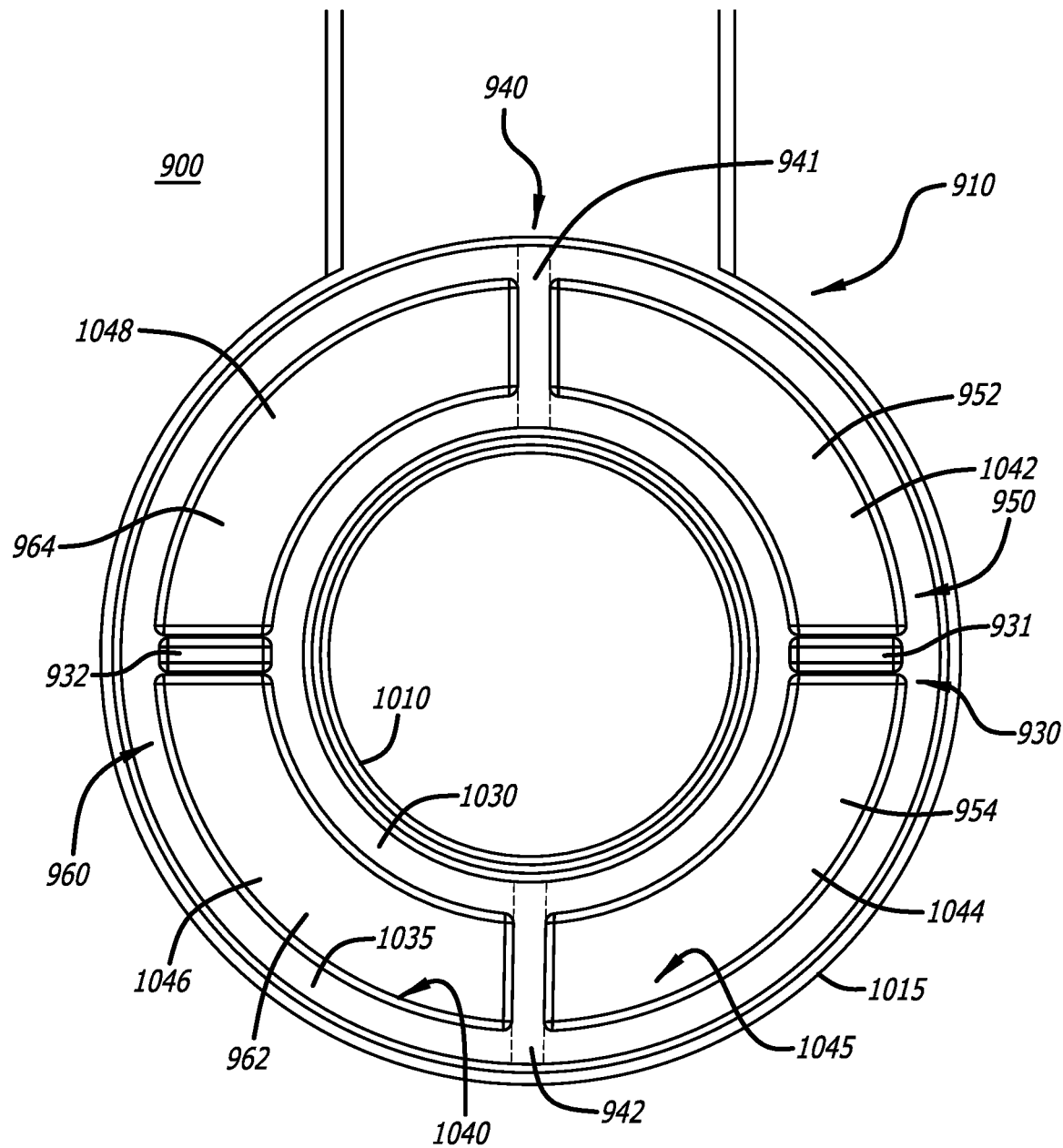
FIG. 10C is a cross-section of the assembled hinge as viewed from a side of the second hinge member towards the first hinge member of FIG. 10B with dampeners installed within end portions of an arc-shaped recessed area (channel) formed within the second hinge member along with the digits of the first hinge member positioned between corresponding dampener pairs.

Similarly, the second hinge member 920 features a second set of digits 940 (e.g., digits 941 and 942) positioned within a housing 945 being an interior area of the second hinge member 920, but the second set of digits 940 may be used to form respective storage channels as shown in FIGS. 10A-10C. Herein, according to this embodiment of the disclosure, the second set of digits 940, namely digits 941 and 942, may be positioned on diametrically opposite sides of the housing 945 to form storage channels, where each storage channel is capable of retaining one or more dampeners made of resiliently compressible material. As shown, the second set of digits 940 (e.g., digits 941 and 942) may be angularly offset from the first set of digits 930 (e.g., digits 931 and 932) of the first hinge member 910.

According to one embodiment of the disclosure, the angular offset between the first set of digits 931-932 and the second set of digits 941-942 may be selected to be around ninety degrees (90°). As a result, where the first set of digits 931/932 are placed at 3:00/9:00 locations, the second set of digits 941/942 are placed at 12:00/6:00 locations. For this illustrative embodiment, quadrants are formed between digits 931/941, 941/932, 932/942 and 942/931. However, it is contemplated that different angular offsets may be selected, which may be positioned at different diametrically opposite positions within the hinge 900 and retain quadrants of the same size or may be positioned at different angular offsets resulting in quadrants of different sizes.

As further shown in FIG. 9, as an illustrative example, a first plurality of dampeners 950, such as dampeners 952 and 954, may be deployed at least within a storage channel formed within the second hinge member 920. A second plurality of dampeners 960, such as dampeners 962 and 964 for example, may be deployed within the same or neighboring storage channel of the second hinge member 920. The first digit 931 of the first hinge member 910 is positioned between the first and second dampener 952 and 954 while the second digit 932 is positioned between third and fourth dampeners 962 and 964. As a result, collective resistance against a motion of dorsiflexion is provided by the first and third dampeners 952 and 962 while the second and fourth dampeners 954 and 964 provide collective resistance against a motion of plantarflexion. As an alternative embodiment, the dampeners 952, 954, 962 and 964 may be deployed within storage channels formed within the first hinge member 910.

When the hinge 900 is assembled in which the second hinge member 920 is interlocked with the first hinge member 910 as shown, rotation of the first hinge member 910 in a direction of ambulation (e.g., counterclockwise "CCW" direction) causes the first set of digits 931 and 932 to rotate in the CCW direction as observed from a medial viewpoint. Such rotation causes a first digit 931 to rotate and compress a first dampener 952 of the first pair of dampeners 950, which is positioned to influence relative dorsiflexion by resisting tibial progression during the patient's gait. As the dampener 952 is made of resiliently compressible material, as the first hinge member 910 rotates in the CCW direction, the movement of the patient's tibia is slowed while the patient's center of gravity is progressed forward over the foot. However, depending on the durometer of at least the dampener 952 (e.g., resistance up to a first prescribed level of compression force), rotation of the first hinge member 910, at some point, would be prevented, thereby resisting or preventing tibial progression and transferring forces to the shin of the patient, thereby creating an extension moment at the knee. Such forces could be used to stabilize mildly weak knees of the patient.

Additionally, the second dampener 954 positioned under the first digit 931 is responsible for resisting the motion of plantarflexion, which occurs at heel strike, during clockwise (CW) rotation of the first hinge member 910 as observed from a medial viewpoint. By resisting motion, this slows the tendency of the foot to rapidly become plantar grade, namely preventing foot slap being a condition normally caused by weakness of the foot and ankle dorsiflexors in which the foot slaps down on the floor with each step.

Besides the first dampener 952 and/or the second dampener 954 described above, it is contemplated that the CCW rotation of the first hinge member 910 further causes the second digit 932 to rotate and compress the third dampener 962 of the second pair of dampeners 960, which is also positioned to influence relative dorsiflexion by resisting tibial progression during the patient's gait. The fourth dampener 964 is also positioned above the digit 932 and is responsible for resisting the motion of plantarflexion, which occurs at heel strike, during rotation of the first hinge member 910.

In summary, as shown in FIG. 9, hinge sections, namely the first and second members 910 and 920 for example, provide a collective housing for internal components that may be arranged to apply resistance against dorsiflexion and/or plantarflexion. For example, dampeners 952 and 962 may be arranged to collectively provide resistance against dorsiflexion motion, such as tibial progression as the patient's center of gravity is progressing forward over the foot. The dampeners 954 and 964 may be arranged to collectively provide resistance against plantarflexion motion. The durometer of the materials forming the dampeners 950, 960 and well as their sizing allows the patient to "tune" the biomechanical properties of the AFO 100 to comport with his or her intended activities such as stiffer and more compression resistant material if the patient is participating in a rigorous activity (e.g., running) and less compression resistant material for walking activities).

Referring now to FIG. 10A, a perspective view of a first embodiment of the first hinge member 910 of the hinge 900 of FIG. 9 is shown. Herein, the first hinge member 910 includes the first set of digits 930 (e.g., digits 931 and 932) positioned on diametrically opposite sections of the housing 935 formed by concentric wall structures 1000, such as 3 o'clock and 9 o'clock positions as shown for illustrative purposes. The concentric wall structures 1000 include a first (inner) wall structure 1010 and a second (outer) wall structure 1015. Although not shown, a bearing for the hinge 900 may be inserted within an opening formed by the first wall structure 1010 and a connecting cap may establish a housing for the assembled hinge.

As shown, the first digit 931 and the second digit 932 protrude from a back surface 1016 of the housing 935 and do not extend the entire width between the concentric wall structures 1010 and 1015. This allows for a third (inner) wall structure 1030 of the second hinge member 920 to be inserted between the first wall structure 1010 and inner ends 1018 and 1019 of the digits 931 and 932 when the hinge 900 is assembled.

Referring to FIG. 10B, a perspective view of a first embodiment of the second hinge member 920 of the hinge 900 of FIG. 9 is shown. Herein, the second hinge member 920 has concentric wall structures 1020, including a third (inner) wall structure 1030 and a fourth (outer) wall structure 1035. These wall structures 1030 and 1035 partially form recessed areas, such as storage channels 1040 and 1045, where the second set of digits 940, namely digits 941 and 942 define the ends of the storage channels 1040 and 1045. Stated differently, the second set of digits 941 and 942 effectively operate as "stops" and separate a recessed area formed by the concentric wall structures 1020 into a first storage channel 1040 and the second storage channel 1045.

As shown in FIG. 10B, the digits 941 and 942 represent ends of the first storage channel 1040, including a first (upper) quadrant 1042 and a second (lower) quadrant 1044 of the first storage channel 1040. One or more dampeners may be installed within the first storage channel 1040. For an assembled hinge 900 with a single dampener deployment to resist dorsiflexion, a dampener may be positioned within the first quadrant 1042 (e.g., situated between the first digit 931 of the first hinge member 910 positioned within the first storage channel 1040 and digit 941). For an assembled hinge 900 with a multi-dampener deployment to control dorsiflexion and plantarflexion, the dampeners may be positioned within the first quadrant 1042 and the second quadrant 1044 (e.g., situated between the digits 941 and 942).

The second set of digits 940 further represent ends of the second storage channel 1045, including a first (lower) quadrant 1046 and a second (upper) quadrant 1048. For free movement without dorsiflexion resistance, no dampeners may be installed within first upper quadrant 1042 within the first storage channel 1040 and the first lower quadrant 1046 within the second storage channel 1045. As the second storage channel 1045 is used to provide additional resistance in conjunction with the resistance provided by the dampeners within the first storage channel 1040, one or more dampeners may be installed within the second storage channel 1045. For example, a single dampener may be positioned within the first quadrant 1046 or the second quadrant 1048 (e.g., between the second digit 932 of the first hinge member and one of the second set of digits 940 of the second hinge member 920). For an assembled hinge 900 with a multi-dampener deployment, the dampeners may be positioned within the first quadrant 1046 and the second quadrant 1048 (e.g., between the second set of digits 941 and 942).

Hence, as described above, dampeners within storage channel areas 1042 and 1046 resist dorsiflexion and tibial progression while providing push off. Dampeners within storage channel areas 1044 and 1048 resist plantarflexion and minimize foot slap.

Referring now to FIG. 10C, a perspective view of an embodiment of a cross-section of the assembled hinge 900 as viewed from the medial side of the hinge 900 is shown, which features the first set of digits 930 (931/932) of the first hinge (lateral) member 910 of FIG. 10A operating with the dampeners 952, 954, 962, 964 installed within arc-shaped storage channels 1040 and 1045 formed by housings 935 and 945 of the second hinge (medial) member 920. Herein the dampeners 952/954 and 962/964 are positioned in quadrants 1042/1044 and 1046/1048 of the storage channels 1040 and 1045. As shown, when the hinge 900 is assembled with the first set of digits 930 (931/932) and the second set of digits 940 (941/942) interacting with the dampeners 952, 954, 962, 964 maintained within recessed areas formed by walled structures 1010, 1015, 1030 and 1035 of the first and second hinge members 910 and 920 (see FIGS. 10A-10B), the digits 931 and 932 of the first hinge member 910 are interposed between dampener pairs 950 and 960 and the second set of digits 940 and 942.

The first digit 931 is positioned between the first dampener 952 and the second dampener 954 of the first dampener pair 950 to provide resistance with respect to tibial progression as the first hinge member 910 is rotated in the direction of ambulation. The first digit 931 of the first hinge member 910 is positioned to further provide resistance with respect to plantarflexion with rotation of the first hinge member 910 (and digit 931) in an opposite direction of ambulation. The second digit 932 is positioned between the third dampener 962 and the fourth dampener 964 of the second dampener pair 960 to provide additional resistance with respect to tibial progression and/or plantarflexion.

As shown in FIG. 10C, the dampeners 952, 954, 962 and/or 964 are removable to allow a clinician or the patient to install dampeners with a desired durometer. In particular, the durometer of dampeners 952, 954, 962 and/or 964 may be installed based on a patient's desired level of activity. For example, where the patient is running or conducting other high impact activities, the dampener 952 may be chosen with a first level of resistance against compression. Alternatively, where the patient is conducting only low-impact activities such as walking, the dampener 952 may be configured with a second level of resistance, which is less than the first level of resistance (e.g., a dampener for running is optimally stiffer than a dampener for walking). The durometer of each of the dampeners 952, 954, 962 and/or 964 may differ to allow a clinician or patient to customize the amount of resistance against dorsiflexion and plantarflexion to improve comfort and ease of motion with respect to the gait of the patient during her or her activity.

In summary, as shown, the dampeners 952, 954, 962 and/or 964 may be configured to operate under compression. The constraint of movement, which is based on a level of stiffness (e.g., level of compression resistance) or the rate of deformation and energy return, may depend on a composition of the dampener. As illustrative examples, dampeners may feature different elastomeric characteristics, varying based on the durometer (stiffness) scale. For example, the dampeners 952 and/or 962 may have the same or different durometer (rigidity level), ranging from prevention of dorsiflexion where the AFO operates closer to a cast with such functionality, various levels of resistance, to free movement where dampener 952 and 962 are not included within the assembled hinge 900. Similarly, the dampeners 954 and/or 964 may have the same or different durometer (rigidity level), ranging from prevention of plantarflexion where the AFO operates closer to a cast with such functionality, various levels of resistance, to free movement where dampener 954 and 964 are not included within the assembled hinge 900.

Herein, the characteristics of any or all of the dampeners 952, 954, 956 and/or 958 (e.g. positioning, durometer, size, etc.) allows a clinician or patient to "tune" the biomechanical properties of the AFO 100 for that particular patient and her or her condition (e.g., greater weight may require greater durometer/rigid characteristics, age may require greater level of dorsiflexion or plantarflexion support, etc.). As further shown, in FIGS. 11A-11C and described below, a composite spring may be configured to operate under compression, where the particular composite and the various dimensions of the spring may be selected to "tune" the degree of movement constraint.

Referring back to FIG. 10C, as an illustrative example, the dampeners 952, 954, 962 and/or 964 may be removed by the patient and substituted with other dampeners of different durometer based on the activity that the patient will be undertaking. This may involve commercialization of specially-design packs of dampeners 952, 954, 962 and/or 964 that are geared towards different activities, where the dampeners 952, 954, 962 and/or 964 may have different durometers to assist in movement by the patient during performance within these activities. For example, the pack may include a single dampener to provide resistance against tibial progression and another dampener to provide resistance against heel strike by controlling the patient's motion of plantarflexion. The pack may include a plurality of dampeners for resistance against tibial progression and/or heel strike, where the dampeners operate collectively in providing resistance against rotation of the digit 931 and/or 932 of the first hinge member 910.

Figure 10D:
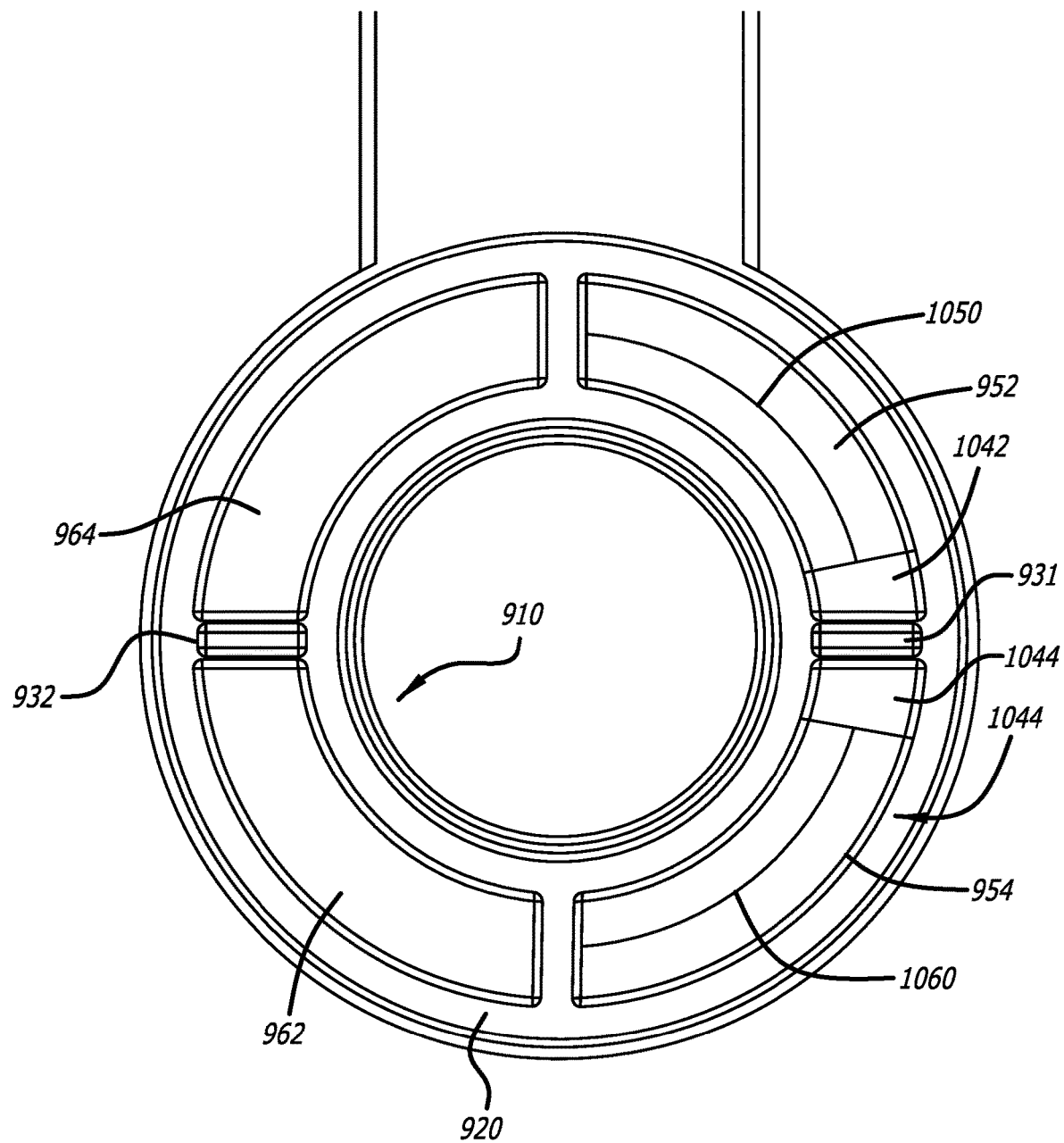
FIG. 10D is a cross-section of the assembled hinge as viewed from a side of the second hinge member towards the first hinge member of FIG. 10B with dampeners that are installed within arc-shaped channel(s) formed within the second hinge member and sized with a desired length to account for a desired degree of free movement or adjust for a desired foot resting position.

Additionally, as shown in FIG. 10D, one or more of the dampeners 952, 954, 962 and/or 964 may be sized to occupy less than an entire quadrant of the store channel reserved for the dampener(s). For example, the dampener 952 may be sized with a shorter radial length 1050 than allocated within the first quadrant 1042 of the second hinge member 920 to allow free movements for a particular distance until the first digit 931 of the first hinge member 910 comes into the contact with the dampener 952 during tibial progression. Additionally, or in the alternative, the dampener 954 may be sized with a shorter radial length 1060 than allocated within the second quadrant 1044 of the second hinge member 920 to allow free movements for a particular distance until the first digit 931 of the first hinge member 910 comes into the contact with the dampener 954 during plantarflexion.

Furthermore, a desired resting position for a foot of the patient, when the AFO 100 is worn, may be set by altering dampener lengths. For example, a change of a prescribed percentage of dorsiflexion may be accomplished by altering dampener lengths across one or more of the digits 931 and 932. This alteration may be accomplished by shortening one dampener (e.g., dampener 952) on one side of the digit 931 (e.g., within the first channel area 1042) and adding another spacer on the other side of the digit 931 or increasing the size of the dampener 954 (not shown) (e.g., within the second storage channel 1044). Spacers could also be preconfigured with a sizing to adjust to angular settings (e.g., 1-20 degrees). The same type of alternations of the lengths of the dampeners 952/954 may be conducted to alter plantarflexion.

Herein, the AFO 900 may be adjusted to allow for tuning the biomechanical functionality associated with the AFO 900. This may be accomplished through modification of the dimensions of the dampeners 952, 954, 956 and/or 958 by virtue of their manufactured length or by adding spacers to effectively increase an overall length of the dampener 952, 954, 956 and/or 958. Thus foot resting position of the foot or ankle may be manipulated/regulated by the length of dampeners 952, 954, 956 and/or 958. This could be done in either direction (dorsiflexion or plantarflexion) with an angular degree of modification up to twenty degrees. Changing the resting angle of the foot/ankle, in addition to regulating the resistance to motion, can regulate the amplitude and timing of ground reaction forces generated when the ankle joint hits its "Stops".

For example, if dorsiflexion dampeners 954 and/or 958 are slightly shortened and plantarflexion dampeners 952 and/or 956 are slightly lengthened the resulting foot resting position could be in slight dorsiflexion. Increased dorsiflexion resting position provides additional toe clearance during swing phase. If plantarflexion dampeners 954 and/or 958 are slightly shortened and dorsiflexion dampeners 952 and/or 956 are slightly lengthened, it would result in a resting position of slight plantarflexion. Increased plantarflexion generates increased push off force as well as knee extension moment/stabilization of the knee during stance phase.

Referring now to FIG. 10E, a perspective view of the assembled hinge 900 identifying ambulatory movement of the patient is shown. Herein, during tibial progression represented by arrow 1070 in accordance with a direction of patient ambulation 1075, the first hinge member 910 rotates in a counterclockwise (CCW) direction as the foot progresses from the heel to the ball of the foot during tibial progression. Given that the assembled hinge 900 may feature a diameter of 1.5-2.5 inches, optional padding 1080 may be positioned on a medial side of the assembled hinge 900 to protect the patient's ankle from contact with a hardened surface.

Figure 10F:
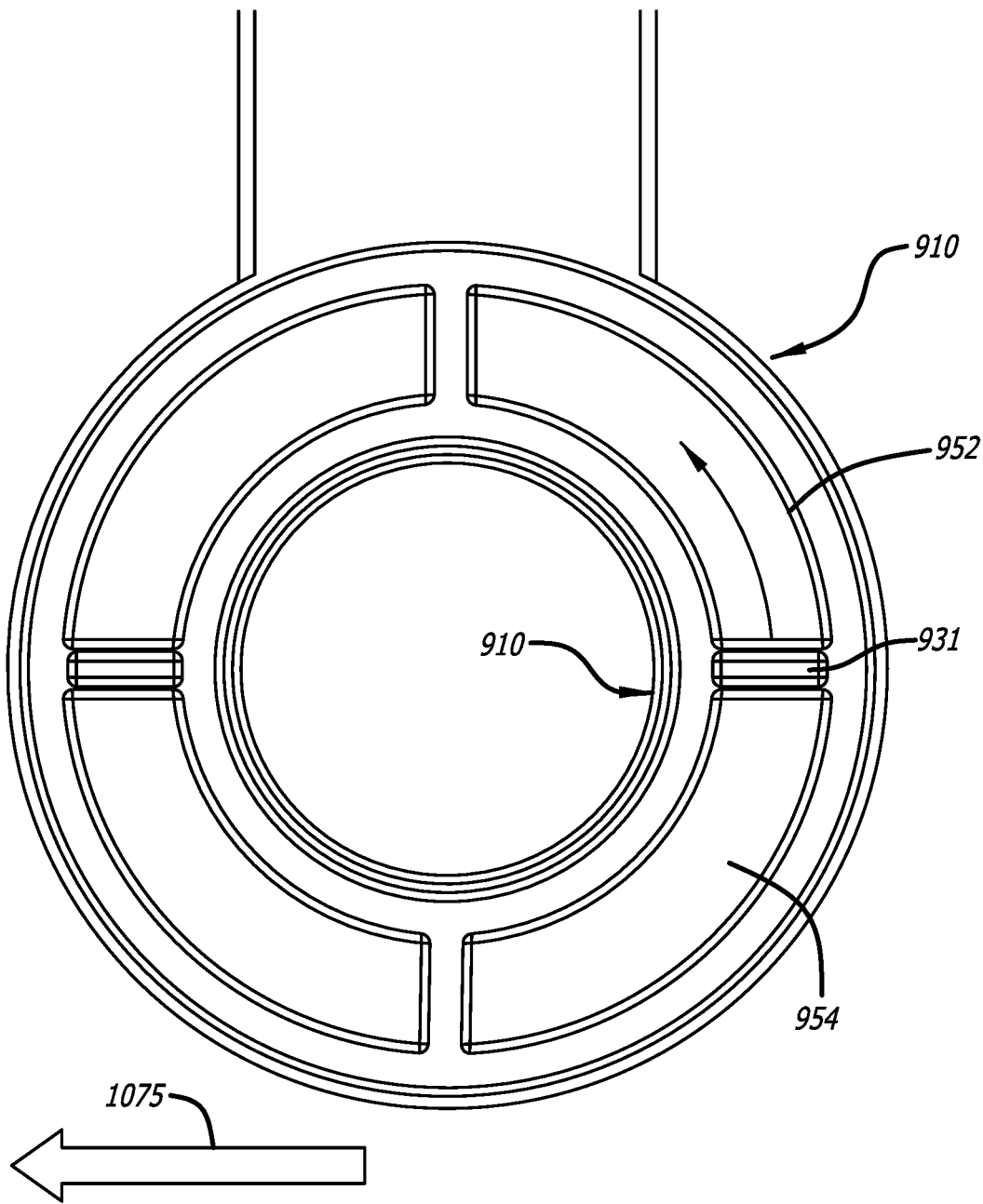
FIG. 10F is a cross-sectional perspective view of the assembled hinge of FIG. 10E identifying movement of a digit of the lateral member in applying forces against a dampener.

As shown in FIG. 10F, during movement in the ambulation direction 1075, the first digit 931 provided by the first hinge member 910 compresses dampener 952, which slows movement of the tibia of the patient to help with stabilizing the knee and provide the patient with better balance. Thereafter, in accordance with the gait of the patient and as the patient rotates from ball of the foot forward and begins swing phase, the first digit 931 will return to its normal position as the dampener 952 decompresses, where dampener 954 maintains sufficient force to neutrally position the foot providing proper toe clearance for the patient throughout swing phase of gait.

III. AFO with Third Hinge Embodiment

Referring now to FIG. 11A, a cross-sectional perspective view of a third embodiment of a hinge 1100 of the AFO of FIG. 1 is shown. As other embodiments, the hinge 1100 features a first hinge member 1110 and a second hinge member 1120. As shown, the first hinge member 1110 operates as a lateral member coupled to the lower leg connector 120 of the AFO 100 while the second hinge member 1120 operates as a medial member coupled to the foot connector 110 of the AFO. Resting between concentric wall structures 1140 and 1145 forming a housing 1130 for the hinge 1100, a C-shaped composite spring 1150 is positioned between a first digit 1112 of the first hinge member 1110 and a single digit 1122 of the second hinge member 1120. Stated differently, the second hinge member 1120 features the digit 1122 upon which a dampener 1160 is positioned on a first side 1114 of the digit 1112 of the first hinge member 1110 while the spring 1150 is positioned on a second side 1116 of the digit 1112. Herein, the composite spring 1150 occupies a majority of a recessed area (e.g., circular channel) 1170 created by the concentric first and second wall structures 1140 and 1145.

Herein, the composite spring 1150 may be removable and interchangeable with other type of composite springs to accommodate for various resistance needs based on a patient's weight and activity level. For example, the composite springs 1150 may be selected with a prescribed level of thickness (or rigidity/resistance) to accommodate for a patient's weight. As an illustrative embodiment, a greater thickness/rigidity for the composite spring 1150 is needed for a patient weighing 200 pounds (lbs.) than a patient weighting 110 lbs. Additionally, or in the alternative, the rigidity/thickness for the composite spring 1150 may be based on a targeted activity of the patient, where the composite spring 1150 may be selected with a greater thickness and/or rigidity for compression resistance to support running than the composite spring 1150 developed to support a less physically demanding activity such as walking.

Figure 11B:
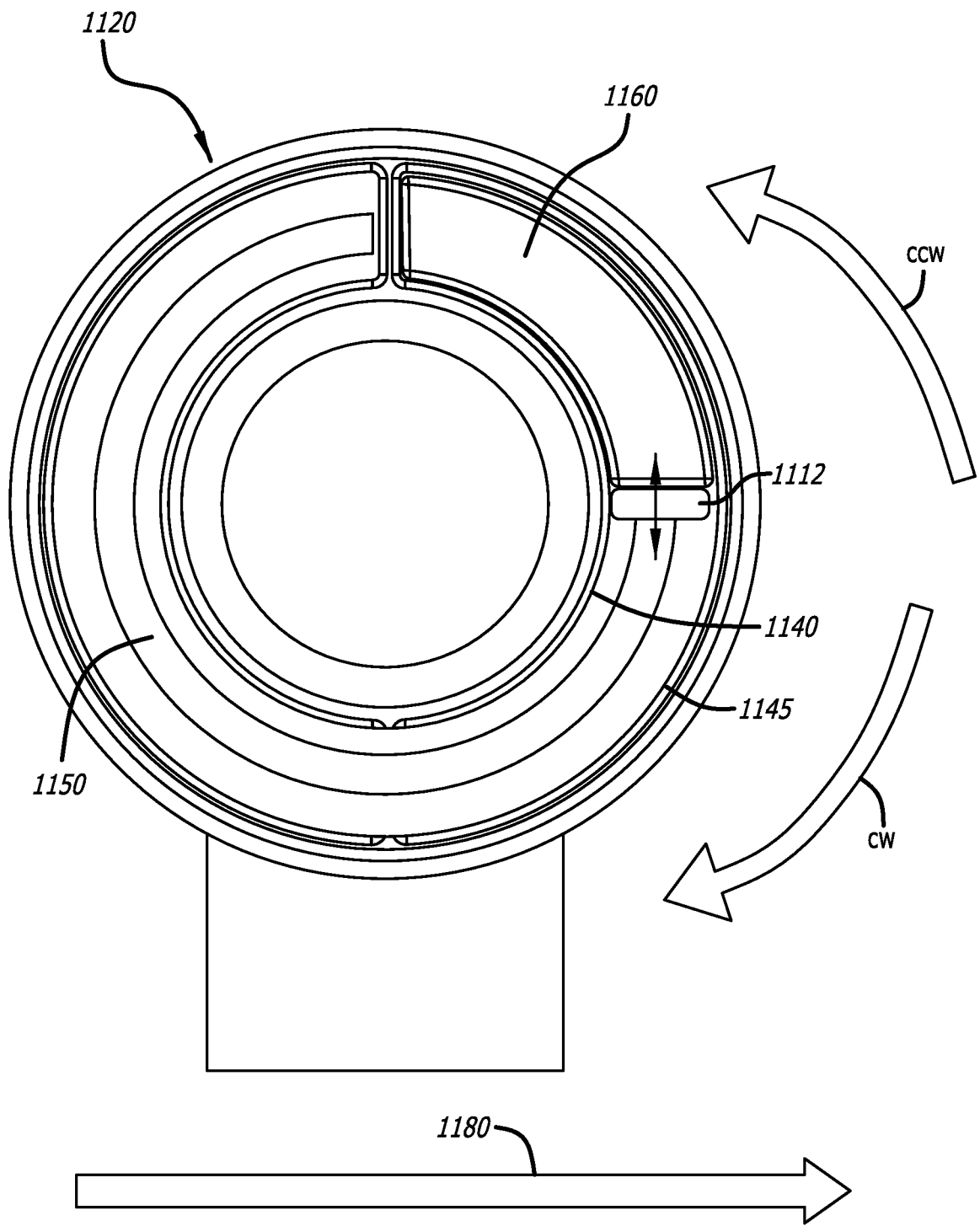
FIG. 11B is a cross-sectional perspective view of the assembled hinge of FIG. 11A identifying movement of a digit of the first hinge (lateral) member in the application of forces against a dampener and responsive recoil of the spring during ambulatory movement by a patient.

As shown in FIGS. 11A-11B, the dampener 1160 is configured to control plantarflexion during movement by the patient while the composite spring 1150 is configured to operate as a dampener by controlling dorsiflexion. More specifically, the dampener 1160 operates as a plantarflexion dampener that is configured to be compressed by the first digit 1112 of the first hinge member 1110 in a CCW direction during a heel strike during a patient's ambulation (tibial progression) as represented by directional arrow 1180. This causes the composite spring 1150 to elongate and move towards the first wall structure 1140. As a build-up to a "toe-off" condition at a late stance phase of a patient's gait, the first digit 1112 moves in the CW direction away from its normal state (steady-state), thereby causing the composite spring 1150 to open and move toward the second wall structure 1145. Then, during a toe-off condition, the string 1150 may provide return energy to provide push-off for the patient's foot. As weight is transferred off the foot, the spring 1150 returns to its resting position (plantar flexes), but the dampener 1160 limits the foot position to neutral, thereby providing toe clearance during gait.

Figure 11C:
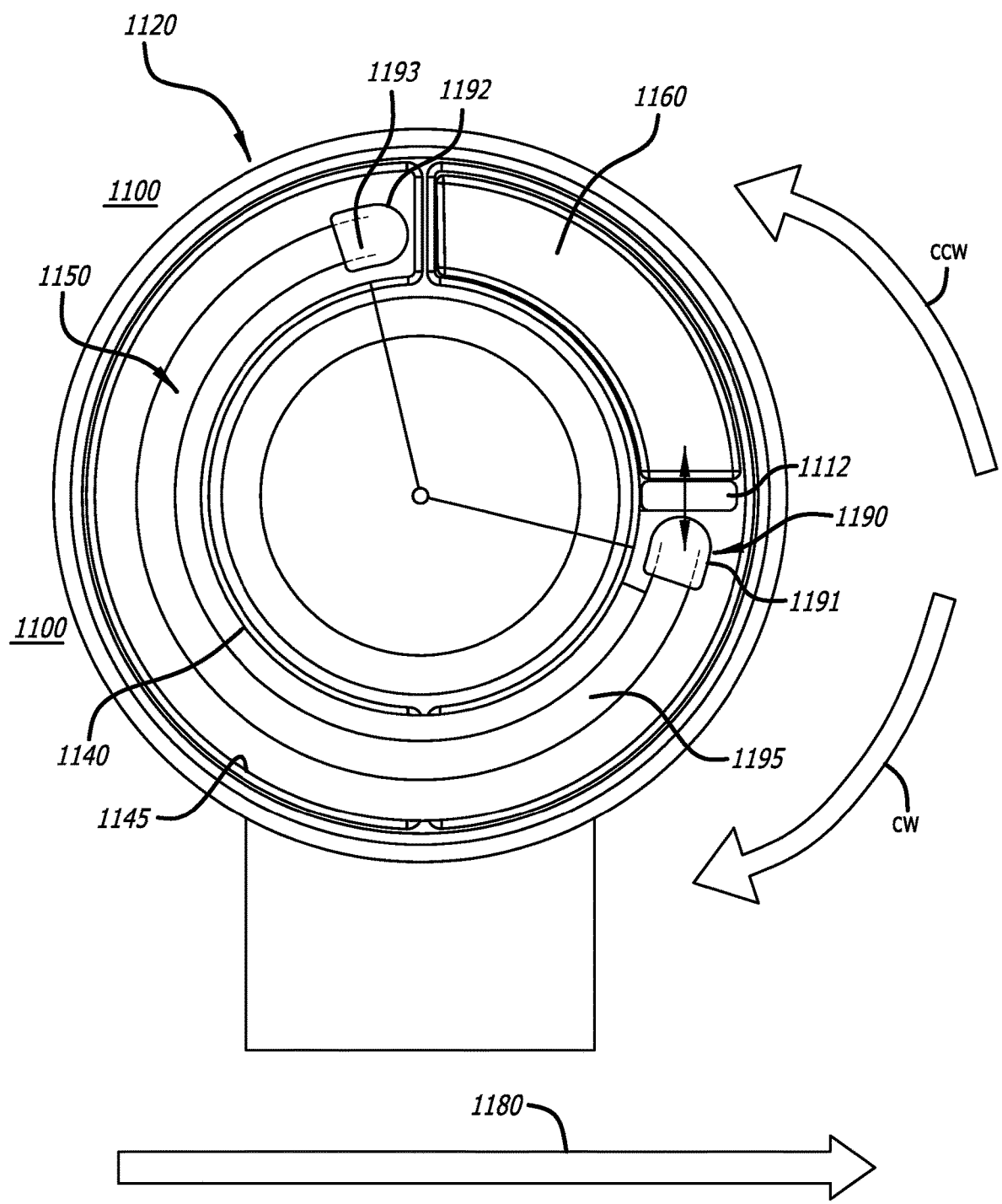
FIG. 11C is a cross-sectional perspective view of the assembled hinge of FIG. 11A identifying an embodiment of the composite spring to ensure continued maintenance in the orientation of the spring within one of the concentric wall structures of a first or second hinge member.

Referring now to FIG. 11C, a cross-sectional perspective view of the assembled hinge 1100 of FIG. 11A identifying an embodiment of the composite spring 1150 to ensure proper orientation within one of the concentric wall structures of a first or second hinge member (e.g., concentric wall structures 1140 and 1145 of the first hinge member 1110. Herein, as shown, ends 1190 and 1192 of the composite spring 1150 may feature a greater width than other sections 1195 of the composite spring 1150. As one illustrative embodiment, the first and second ends 1190 and 1192 of the composite spring 1150 may be inserted into corresponding end caps 1191 and 1193 filled with an elastomer. Hence, the end caps 1191 and 1193 provide shock absorbing characteristics. As another illustrative embodiment, the first and second ends 1190 and 1192 of the composite spring 1150 may be inserted into slots formed within the end caps 1191 and 1193, where the end caps 1191 and 1193 are made of hardened plastic, silicon, or other material capable of withstanding continuous compression forces between exerted upon and removed during patient ambulation.

Herein, the greater width provided proximate to the first and second end 1190 and 1192 of the composite spring 1150 restricts lateral movement of the spring 1150 in response to compression and decompression caused by CW and CCW movement of the first digit 1112. Such restricted lateral movement maintains the composite spring 1150 at a desired position, thereby avoiding the composite spring 1150 becoming misaligned, which may adversely the operability of the AFO based on lesser resistance and/or return energy provided by the composite spring 1150.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. For example, while the first and second members forming the hinge are represented as lateral and medial members for illustrative purposes, it is contemplated that the structure of these members may be reversed where the lateral member remains static and the medial member rotates. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An ankle foot orthosis, comprising:
   a lower leg connector;
   a foot connector; and
   a hinge functionally interposed between the lower leg connector and the foot connector, the hinge including a first hinge member interlocked with a second hinge member,
   wherein the first hinge member includes at least a first digit moveable between at least a first stop formed as part of the second hinge member,
   wherein the second hinge member includes a first recessed area and a second recessed area, the first recessed area is configured to retain at least a first dampener adapted to resist a positional change of the foot connector to prevent excessive plantarflexion or dorsiflexion of a foot of a patient and the second recessed area is configured to retain a composite spring positioned between a second side of the first digit and the first stop while the first dampener is positioned on a first side of the first digit, and
   wherein the composite spring is compressed and opened in response to movement of the first digit in a second direction opposite a first direction and is configured to provide return energy in response to movement of the first digit back in the first direction in response to a push-off of the foot of the patient.

2. The ankle foot orthosis of claim 1, wherein the first dampener is made of resiliently compressible material being at least one of a rubber, a foam or a plastic.

3. The ankle foot orthosis of claim 1, wherein the first dampener operates as a plantarflexion dampener that is configured to be compressed by the first digit of the first hinge member in the first direction in response to a heel strike during ambulation of a patient wearing the ankle foot orthosis.

4. The ankle foot orthosis of claim 1, wherein the composite spring is removable and interchangeable to substitute the composite spring for a second composite spring configured with either greater resistance to account for patient weight or a targeted activity level.

5. The ankle foot orthosis of claim 1, wherein the first dampener is exchangeable to provide different levels of resistance based on a resiliently compressible material of the first dampener.

6. The ankle foot orthosis of claim 1, wherein the first dampener made of a first resiliently compressible material is removable from the second hinge member and exchangeable with a second dampener made of a second resiliently compressible material having a greater or lesser level of resistance based on a desired activity of a patient wearing the ankle foot orthosis.

7. The ankle foot orthosis of claim 1, wherein the first dampener is sized less than the second recessed area so that the first digit refrains from coming into contact and engaging with the first dampener in response to rotational movement of the first hinge member in a direction of ambulation until after a prescribed movement of the first digit upon which the first digit engages and compresses the first dampener to resist tibial progression.

8. The ankle foot orthosis of claim 1, wherein a resiliently compressible material is attached to an external surface of the first digit.

9. The ankle foot orthosis of claim 1, wherein the first digit may be repositioned by altering lengths of at least one of the first dampener to set a desired resting position of the foot of the patient during use.

10. The ankle foot orthosis of claim 1, wherein a length of the first dampener may be shortened and a spacer may be inserted within the first recessed area.

11. A method of adjusting an ankle foot orthosis to a patient, the orthosis having a hinge functionally interposed between a lower leg connector and a foot connector, and having at least a first digit moveable between a first stop and a second stop, the method comprising:
   separating a first hinge member and a second hinge member of the hinge;
   inserting a first spacer between the first digit and the first stop, and a second spacer between the first digit and the second stop; and
   assembling the first hinge member and the second hinge member,
   wherein the second hinge member includes a first recessed area and a second recessed area, the first recessed area is configured to retain at least the first spacer being a first dampener adapted to resist against excessive plantarflexion or dorsiflexion of a foot of a patient and the second recessed area is configured to retain the second spacer being a composite spring positioned between a second side of the first digit and the first stop while the first dampener is positioned on a first side of the first digit, and
   wherein the composite spring is compressed and opened in response to movement of the first digit in a second direction opposite a first direction and is configured to provide return energy in response to movement of the first digit back in the first direction in response to a push-off of the foot of the patient.

12. The method of adjusting the ankle foot orthosis of claim 11, wherein the first spacer and the second spacer are configured to resist movement of the lower leg connector and the foot connector associated with controlling dorsiflexion and plantarflexion.

13. The method of adjusting the ankle foot orthosis of claim 11, further comprising:
   disassembling the hinge to separate the first hinge member from the second hinge member;
   removing the first spacer from the second hinge member; and
   inserting a substitute spacer for the first spacer, wherein the substitute spacer features a different durometer than the first spacer to provide lesser or greater resistance in movement of the lower leg connector and the foot connector associated with controlling dorsiflexion and plantarflexion.

14. The method of adjusting the ankle foot orthosis of claim 11, wherein the second stop is the same structural element as the first stop.

15. The method of adjusting the ankle foot orthosis of claim 11, further comprising selecting the first spacer among multiple different arms as a function of a desired resilient compressibility in the hinge.

16. The method of adjusting the ankle foot orthosis of claim 11, further comprising selecting the first spacer among multiple different arms as a function of a desired maximum spacer movement in the hinge.

17. The method of adjusting the ankle foot orthosis of claim 11, further comprising selecting the first spacer among multiple different arms as a function of a desired amount of damping in the hinge.

18. The method of adjusting the ankle foot orthosis of claim 11, wherein the first hinge member includes the first digit and a second digit moveable between third and fourth stops, and further comprising inserting a third spacer between the second digit and the third stop, and a fourth spacer between the second digit and the fourth stop.

19. The method of adjusting the ankle foot orthosis of claim 11, wherein the inserting of the first spacer and the second spacer comprise inserting a component including a first, second, third and fourth arms positioned between the first digit, a second digit, the first stop and the second stop.

20. An ankle foot orthosis comprising:
a lower leg connector;
a foot connector; and
a hinge functionally interposed between the lower leg connector and the foot connector, the hinge including a first hinge member interlocked with a second hinge member,
wherein the first hinge member includes at least a first digit moveable between at least a first stop formed as part of the second hinge member, and
wherein the second hinge member further includes (i) a first recessed area configured to retain at least a first dampener positioned adjacent to the first digit and a second dampener and (ii) a second recessed area configured to retain a third dampener and a fourth dampener and a second digit is interposed between the third dampener and the fourth dampener.

21. The ankle foot orthosis of claim 20, further comprising a spider having a first arm positioned between the first digit and the first stop and a second arm positioned between the first digit and a second stop.

22. The ankle foot orthosis of claim 21, further comprising a spider having a third arm positioned between a second digit and the second stop and a fourth arm positioned between the second digit and the first stop.

23. The ankle foot orthosis of claim 22, wherein at least one of the first arm, the second arm, the third arm, and the fourth arm of the spider comprise a resiliently compressible material providing compressibility by at least 1 degree.

24. The ankle foot orthosis of claim 21, wherein at least one of the first arm and the second arm of the spider comprise a resiliently compressible material providing compressibility by at least 1 degree.

25. The ankle foot orthosis of claim 20, wherein rotational movement of the first hinge member in a direction of ambulation causes compression of the first dampener to resist tibial progression when the ankle foot orthosis is worn by a patient.

26. The ankle foot orthosis of claim 25, wherein rotational movement of the first hinge member in a direction opposite the direction of ambulation causes compression of the second dampener to resist a motion of plantarflexion when the ankle foot orthosis is worn by the patient.

27. A method of controlling dorsiflexion and plantarflexion through an ankle foot orthosis having a hinge functionally interposed between a lower leg connector and a foot connector and the hinge including a first hinge member including a first digit and a second hinge member including a stop and a recessed area, the method comprising:
a inserting a first spacer between the first digit and the stop and a second spacer a between the first digit and the stop, the first spacer corresponds to a first dampener configured to control plantarflexion and resist a positional change of the foot connector and the second spacer corresponds to a composite spring configured to control dorsiflexion,
wherein the composite spring is (i) positioned between a second side of the first digit, (ii) compressed and opened in response to movement of the first digit in a second direction opposite a first direction, and (iii) configured to provide return energy in response to movement of the first digit back in the first direction in response to a push-off of the foot of the patient, and
assembling the first hinge member and second hinge member to form the hinge.

28. The method of controlling dorsiflexion and plantarflexion through the ankle foot orthosis of claim 27, further comprising:
disassembling the hinge to separate the first hinge member from the second hinge member;
removing the first spacer or the second spacer from the second hinge member; and
inserting a substitute spacer for the first spacer or the second, wherein the substitute spacer features a different durometer than (i) the first spacer to provide lesser or greater resistance in movement of the lower leg connector and the foot connector associated with controlling plantarflexion or (ii) the second spacer to provide a lesser or greater resistance in movement of the lower leg connector and the foot connector associated with controlling dorsiflexion.

29. An ankle foot orthosis comprising:
a lower leg connector;
a foot connector; and
a hinge functionally interposed between the lower leg connector and the foot connector, the hinge including a first hinge member interlocked with a second hinge member, wherein the first hinge member includes at least a first digit moveable between at least a first stop formed as part of the second hinge member, and
a first resiliently compressible material that provides at least 1 degree of play when the first digit is juxtaposed against the first stop, and a second resiliently compressible material that provides at least 1 degree of play when the first digit is juxtaposed against a second stop formed as part of the second hinge member, and the first resiliently compressible material has a different amount of play than the second resiliently compressible material for the same force.

* * * * *